United States Patent [19]
Santoli et al.

[11] Patent Number: 5,702,702
[45] Date of Patent: Dec. 30, 1997

[54] MODIFIED CYTOTOXIC TALL CELL LINE AND COMPOSITIONS AND METHODS FOR MANUFACTURE AND USE THEREOF AS THERAPEUTIC REAGENTS FOR CANCER

[75] Inventors: Daniela Santoli; Giovanni Rovera, both of Bryn Mawr; Alessandra Cesano, Philadelphia, all of Pa.

[73] Assignee: The Wistar Institute of Anatomy and Biology, Philadelphia, Pa.

[21] Appl. No.: 472,686

[22] Filed: Jun. 6, 1995

Related U.S. Application Data

[63] Continuation-in-part of Ser. No. 374,289, Jan. 18, 1995, which is a continuation-in-part of Ser. No. 63,188, May 14, 1993, abandoned, which is a continuation-in-part of Ser. No. 859,927, Mar. 30, 1992, Pat. No. 5,272,082.

[51] Int. Cl.$^6$ .............. A01N 63/00; C12N 5/00; C12N 5/08; A61K 31/00
[52] U.S. Cl. ............ 424/93.71; 424/93.1; 424/93.2; 424/93.21; 424/93.7; 424/534; 435/2; 435/366; 435/372; 435/372.3; 514/2; 514/9; 514/10; 514/885; 552/577; 552/576; 552/581
[58] Field of Search .................. 424/93.1, 93.2, 424/93.21, 93.7, 93.71, 534; 435/2, 240.1, 240.2, 366, 372, 372.3; 514/2, 9, 10, 885; 552/577, 576, 581

[56] References Cited

U.S. PATENT DOCUMENTS

| | | | |
|---|---|---|---|
| 5,166,059 | 11/1992 | Pastan et al. | 435/69.7 |
| 5,272,082 | 12/1993 | Santoli et al. | 435/372.3 |

OTHER PUBLICATIONS

Cesano et al., Canc. Res., 56: 3021–3029, 1996.
Boon, Int. J. Cancer, 54: 177–180, 1993.
Osband et al., Imm. Today, 11: 103–105, 1990.
Foon, Canc. Res., 49:1621–39, 1989.

S. Chan et al., "Mechanism of Interferon–Induction by Natural Killer Cell Stimulatory Factor (NKSF): Role of Transcription and mRNA Stability in the Synergistic Interactions Between NKSF and Interleukin–2 or Phorbal Diesters", *J. Immunol.*, 148(1):92–98 (Jan. 1, 1992).

D. Santoli et al., "Synergistic and Antagonistic Effects of IL–1 and IL–4, Respectively, on the IL–2–Dependent Growth of a T Cell Receptor–Human T Leukemia Cell Line", *J. Immunol.*, 144(12):4703–4711 (Jun. 15, 1990).

R. O'Connor et al., "Growth Factor–Dependent Differentiation Along the Myeloid and Lymphoid Lineages in an Immature Acute T Lymphocytic Leukemia", *J. Immunol.*, 145(11):3779–3787 (Dec. 1, 1990).

R. O'Connor et al., "Growth Factor Requirements of Childhood Acute T–Lymphoblastic Leukemia: Correlation Between Presence of Chromosomal Abnormalities and Ability to Grow Permanently in Vitro", *Blood*, 77(7):1534–1545 (Apr. 1, 1991).

A. Cesano et al., "Homing and Progression Patterns of Childhood Acute Lymphoblastic Leukemias in Severe Combined Immunodeficiency Mice", *Blood*, 77(11):2463–2474 (Jun. 1, 1991).

(List continued on next page.)

*Primary Examiner*—Ronald B. Schwadron
*Attorney, Agent, or Firm*—Howson and Howson

[57] ABSTRACT

The invention provides a modified human cytotoxic T cell line, which is characterized by dual activity in vitro and in vivo against malignant cells and virus-infected cells. Also provided are effective and safe methods for use of the modified cells in adoptive therapy of cancer and untreatable vital diseases in MHC-mismatched recipients, and in marrow purging to achieve complete eradication of residual tumor cells from marrows of patients with leukemia and other types of cancer. Also provided are effective and safe methods for use of the cytokine stimulated, irradiated TALL-104 cells in the manufacture of a veterinary composition for adoptive therapy of canine and feline malignancies.

8 Claims, 18 Drawing Sheets

OTHER PUBLICATIONS

A. Cesano et al, "Establishment of a Karyotypically Normal Cytotoxic Leukemic T–Cell Line from a T–All Sample Engrafted in SCID Mice", *Blood*, 81(10):2714–2722 (May 15, 1993).

A. Cesano et al, "Effect of Human Interleukin 3 on the Susceptibility of Fresh Leukemia Cells to Interleukin–2–Induced Lymphokine Activated Killing Activity", *Leukemia*, 6(6):567–573 (Jun., 1992).

A. Cesano et al, "Cytokine Modulation of the Susceptibility of Acute T–Lymphoblastic Leukemia Cell Lines to LAK Activity", *Leukemia*, 7(3):404–409 (Mar., 1993).

A. Cesano et al, "Mechanisms of MHC–Non–Restricted Lysis in Two Human Killer T Cell Lines", *Nat. Immun.*, 11(5):288–289 (Oct., 1992).

A. Cesano et al, "Two Unique Human Leukemic T–Cell Lines Endowed with a Stable Cytotoxic Function and a Different Spectrum of Target Reactivity Analysis and Modulation of Their Lytic Mechanisms", *In Vitro Cell Dev. Biol.*, 28A:648–656 (Sep.–Oct., 1992).

A. Cesano et al, "Inducible Expression of Granulocyte–Macrophage Colony–Stimulating Factor, Tumor Necrosis Factor–, and Interferon–in Two Human Cytotoxic Leukemic T–Cell Lines", *In Vitro Cell Dev. Biol.*, 28A:657–662 (Sep.–Oct., 1992).

A. Cesano et al, "The Severe Combined Immunodeficient (SCID) Mouse as a Model for Human Myeloid Leukemias", *Oncogene*, 7:827–836 (May, 1992).

A. Cesano et al, "Treatment of Experimental Glioblastoma with a Human Major Histocompatibility Complex Nonrestricted Cytotoxic T Cell Line", *Cancer Research*, 55:96–101 (Jan. 1, 1995).

A. Cesano et al, "An Effective and Safe Marrow Purging Strategy Using a Lethally Irradiated Killer T Cell Clone", in *Advances in Bone Marrow Purging and Processing*, Fourth International Symposium, pp. 165–173 (Oct. 1994).

A. Cesano et al, "Cellular and Molecular Mechanisms of Activation of MHC Nonrestricted Cytotoxic Cells by IL–12", *J. Immunology*, 151:2943–2957 (Sep., 1993).

P. Greenberg et al, "Effector Mechanisms Operative in Adoptive Therapy of Tumor–Bearing Animals: Implications for the Use of Interleukin–2", *J. Biol. Resp. Modifiers*, 3(5):455–461 (1984).

J. Klarnet et al, "Helper–Independent CD8+ Cytotoxic T Lymphocytes Express IL–1 Receptors and Require IL–1 for Secretion of IL–2", *J. Immunol.*, 142(7):2187–2191 (Apr. 1, 1989).

M. Cheever et al., "Potential Uses of Interleukin 2 in Cancer Therapy", *Immunobiol.*, 172:365–382 (1986).

"First AIDS Gene–Transfer Clinical Comes Before RAC", *Biotechnology Newswatch*, 11(22):1–3 (Nov. 18, 1991).

"RAC Phases Out Human Gene Therapy Unit; Approves Six New Protocols", *Biotechnology Newswatch*, 12(4):9–10 (Feb. 17, 1992).

D. Ojcius et al, "Cell–Mediated Killing: Effector Mechanisms and Mediators", *Cancer Cells*, 2(5):138–145 (May, 1990).

E. Grimm et al, "Lymphokine–Activated Killer Cell Phenomenon: Lysis of Natural Killer–Resistant Fresh Solid Tumor Cells by Interleukin 2–Activated Autologous Human Peripheral Blood Lymphocytes", *J. Exp. Med.*, 155:1823–1841 (Jun., 1982).

S. Rosenberg, "Lymphokine–Activated Killer Cells: A New Approach to Immunotherapy of Cancer", *J. Natl. Can. Inst.*, 75(4):595–603 (Oct., 1985).

S. Rosenberg et al, "Special Report—Observations on the Systemic Administration of Autologous Lymphokine–Activated Killer Cells and Recombinant Interleukin–2 to Patients with Metastatic Cancer", *New Engl. J. Med.*, 313(23):1485–1492 (Dec. 5, 1985).

S. Rosenberg et al, "A Progress Report on the Treatment of 157 Patients with Advanced Cancer Using Lymphokine–Activated Killer Cells and Interleukin–2 or High–Dose Interleukin–2 Alone", *New Engl. J. Med.*, 316(15):889–897 (Apr. 9, 1987).

S. Rosenberg, "What's New in General Surgery: The Development of New Immunotherapies for the Treatment of Cancer Using Interleukin–2", *Ann. Surg.*, 208(2):121–135 (Aug., 1988).

S. Rosenberg et al, "Experience with the Use of High–Dose Interleukin–2 in the Treatment of 652 Cancer Patients", *Ann. Surg.*, 210(4):474–485 (Oct., 1989).

M. Rosenstein et al, "Lymphokine–Activated Killer Cells: Lysis of Fresh Syngeneic Natural Killer–Resistant Murine Tumor Cells by Lymphocytes Cultured in Interleukin 2", *Cancer Res.*, 44:1946–1953 (May, 1984).

J. Mule et al, "Adoptive Immunotherapy of Established Pulmonary Metastases with LAK Cells and Recombinant Interleukin–2", *Science*, 225:1487–1489 (Sep. 28, 1984).

R. Lafreniere et al, "Successful Immunotherapy of Murine Experimental Hepatic Metastases with Lymphokine–Activated Killer Cells and Recombinant Interleukin 2", *Cancer Res.*, 45:3735–3741 (Aug., 1985).

A. Mazumder et al, "Successful Immunotherapy of Natural Killer–Resistant Established Pulmonary Melanoma Metastases by the Intravenous Adoptive Transfer of Syngeneic Lymphocytes Activaed in vitro by Interleukin 2", *J. Exp. Med.*, 159:495–507 (Feb., 1984).

W. West et al, "Constant–Infusion Recombinant Interleukin–2 in Adoptive Immunotherapy of Advanced Cancer", *New Engl. J. Med.*, 316(15):898–905 (Apr. 9, 1987).

S. Topalian et al, "Expansion of Human Tumor Infiltrating Lymphocytes for use in Immunotherapy Trials"*J. Immunol. Meth.*, 102:127–141 (1987).

J. Mule et al, "Immunotherapy with Lymphokine Combinations", *Important Adv. in Oncol.*, 10:99–126 (1989).

K. Itoh et al, "Interleukin 2 Activation of Cytotoxic T–Lymphocytes Infiltrating into Human Metastatic Melanomas", *Cancer Res.*, 46:3011–3017 (Jun., 1986).

R. Lee et al, "Cardiorespiratory Effects of Immunotherapy with Interleukin–2", *J. Clin. Oncol.*, 7(1):7–20 (Jan., 1989).

M. Lotze et al, "Mechanisms of Immunologic Antitumor Therapy: Lessons from the Laboratory and Clinical Applications", *Hum. Immunol.*, 28:198–207 (1990).

J. Gootenberg et al, "A Biochemical Variant of Human T Cell Growth Factor Produced by a Cutaneous T Cell Lymphoma Cell Line", *J. Immunol.*, 129(4):1499–1505 (Oct., 1982).

S. Arya et al, "T–Cell Growth Factor Gene: Lack of Expression in Human T–Cell Leukemia–Lymphoma Virus–Infected Cells", *Science*, 223:1086–1087 (Mar., 1984).

Y. Kaufmann et al, "Interleukin 2 Induces Human Acute Lymhocytic Leukemia Cells to Manifest Lymphokine–Activated–Killer (LAK) Cytotoxicity", *J. Immunol.*, 139(3):977–982 (Aug., 1, 1987).

A. Kasid et al, "Human Gene Transfer: Characterization of Human Tumor–Infiltrating Lymphocytes as Vehicles for Retroviral–Mediated Gene Transfer in Man", *Proc. Natl. Acad. Sci. USA*, 87:473–477 (Jan., 1990).

K. Nishihara et al "Augmentation of Tumor Targeting in a Line of Glioma–specific Mouse Cytotoxic T–Lymphocytes by Retroviral Expression of Mouse–Interferon Complementary DNA", *Cancer Research*, 48:4730–4735 (Sep. 1, 1988).

H. Karasuyama et al, "Autocrine Growth and Tumorigenicity of Interleukin 2–Dependent Helper T Cells Transfected with IL–2 Gene", *J. Exp. Med.*, 169:13–25 (Jan., 1989).

T. Torigoe et al, "Interleukin 4 Inhibits IL–2–Induced Proliferation of a Human T–Leukemia Cell Line without Interfering with p56–LCK Kinase Activation", *Cytokine*, 4(5):369–376 (Sep., 1992).

T. Torigoe et al, "Interleukin–3 Regulates the Activity of the LYN Protein–Tyrosine Kinase in Myeloid–Committed Leukemic Cell Lines", *Blood*, 80(3):617–624 (Aug. 1, 1992).

B. Perussia et al, "Natural Killer (NK) Cell Stimulatory Factor or IL–12 has Differential Effects on the Proliferation of TCR–, TCR–T Lymphocytes, and NK Cells", *J. Immunol.*, 149(11):3495–3502 (Dec. 1, 1992).

B. Lange et al, "Pediatric Leukemia/Lymphoma with t(8;14) (q24;q11)", *Leukemia*, 6(7):613–618 (Jul., 1992).

T. Han et al, "Stimulatig Capacity of Blast Cells from Patients with Chronic Myelocytic Leukaemia, in Blastic Crisis in One–Way Mixed Lymphocyte Reaction: Lack of Evidence for T Lymphoblastic Conversion", *Immunology*, 35:299–305 (1978).

B. Rouse et al, "Consequences of Exposure to Ionizing Radiation for Effector T Cell Function in Vivo", *Viral Immunology*, 2(2):69–78 (1989).

A. Stern et al, "Purification to Homogeneity and Partial Characterization of Cytotoxic Lymphocyte Maturation Factor from Human B–Lymphoblastoid Cells", *Proc. Natl. Acad. Sci. USA*, 87:6808–6812 (Sep., 1990).

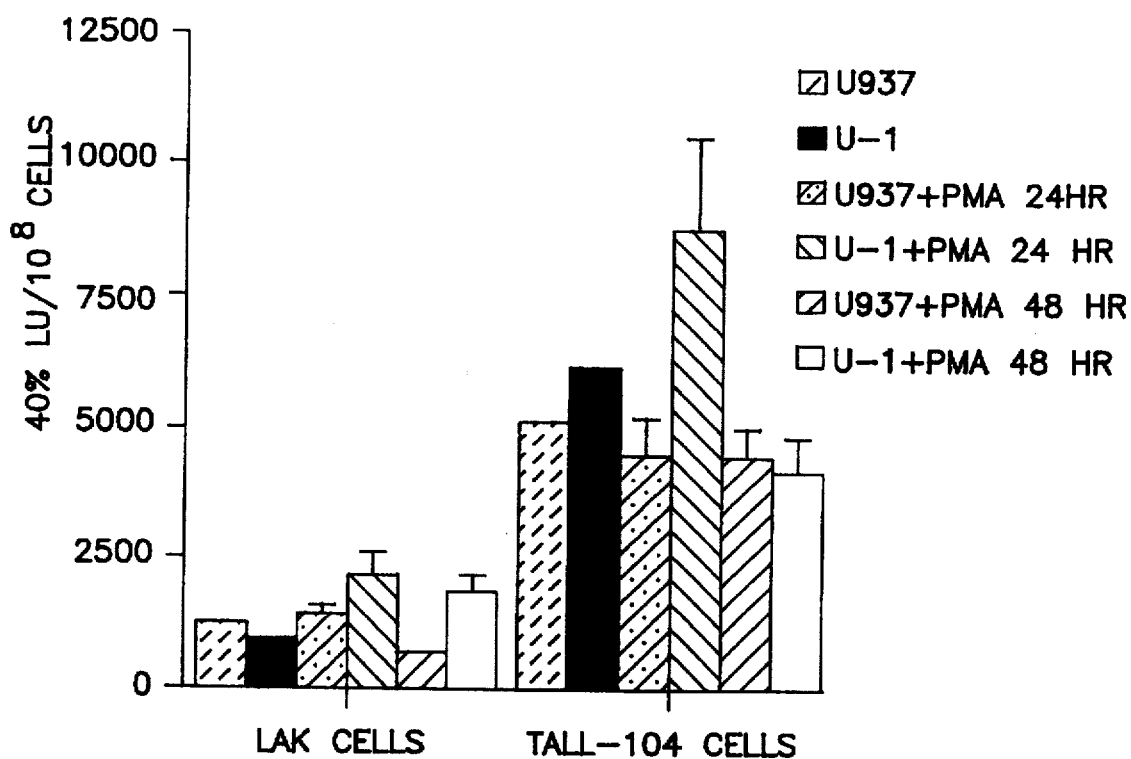
FIG. IA
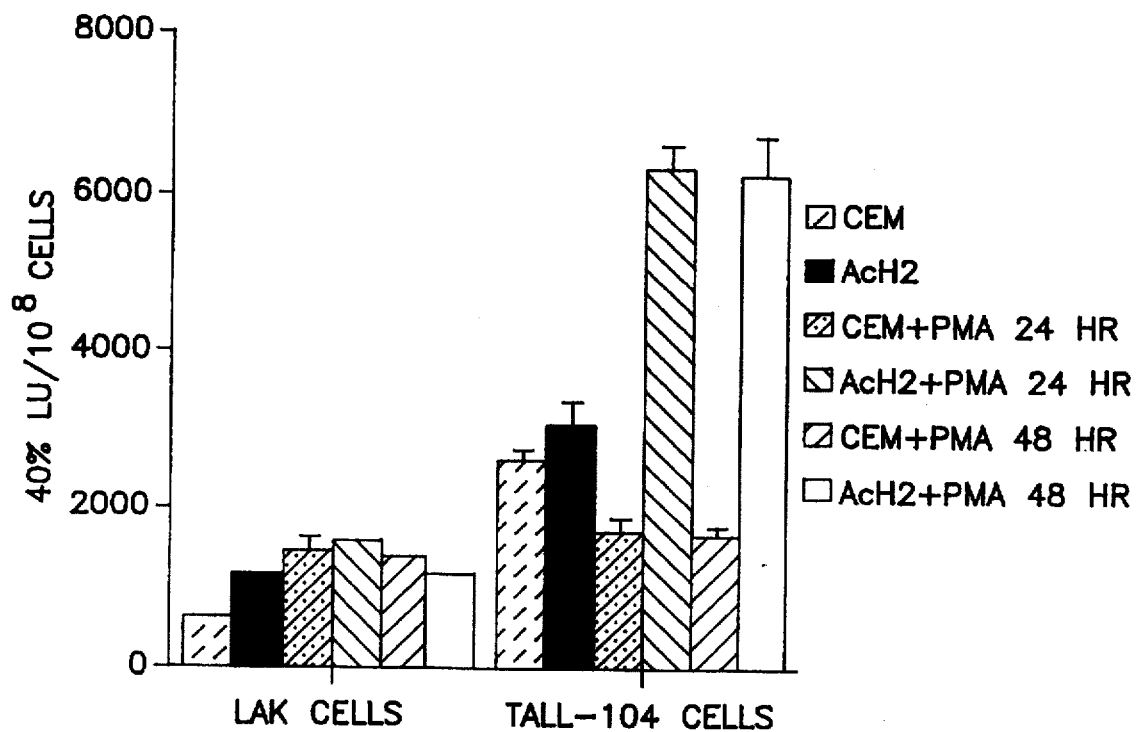
FIG. IB

MODIFIED CYTOTOXIC TALL CELL LINE AND COMPOSITIONS AND METHODS FOR MANUFACTURE AND USE THEREOF AS THERAPEUTIC REAGENTS FOR CANCER

CROSS-REFERENCE TO RELATED APPLICATIONS

This is a continuation-in-part of pending U.S. patent application Ser. No. 08/374,289, filed Jan. 18, 1995, which is a continuation-in-part of U.S. patent application Ser. No. 08/063,188, filed May 14, 1993, now abandoned which was a continuation-in-part of U.S. patent application Ser. No. 07/859,927, filed March 30, 1992, now U.S. Pat. No. 5,272,082. These parent applications are incorporated by reference herein.

This invention has been made with the financial assistance of Grants CA-47589, CA-10815, and CA-42232 from the National Institutes of Health. The United States government has certain rights in this invention.

FIELD OF THE INVENTION

This invention relates generally to the modified cytotoxic T lymphoblastic leukemia (T-ALL) cell line and its therapeutic uses.

BACKGROUND OF THE INVENTION

Cytolytic T lymphocytes (CTL) and natural killer (NK) cells have complementary roles in providing defense against tumor cells, virus-infected cells and other invading agents [see, e.g., Oycius and Young, Cancer Cells 2:138 (1990)]. CTL are $CD3^+$/T-cell receptor (TCR) $\alpha\beta^+$, $CD8^+$, $CD16^-$ cells which recognize specific peptides in association with class I molecules of the major histocompatibility complex (MHC). NK cells are $CD3^-$/$TCR^-$, $CD16^+$, $CD56^+$ cells which are constitutively able to lyse virus-infected cells and some tumor cell lines (but not fresh tumor cells) without prior sensitization and without restriction by MHC antigens. The molecules specifically involved in target cell recognition by NK cells (the putative NK receptor) are as yet unknown.

Over the past decade, lymphokine-activated killer (LAK) activity has been defined as an additional type of MHC non-restricted killing. LAK cells are conventionally generated upon short-term culture of human peripheral blood cells in interleukin-2 (IL-2) and possess phenotypic characteristics of either NK ($CD3^-CD16^+$) or T ($CD3^+CD16^-$) cells, thus constituting an heterogeneous (mixed) cell population. LAK cells are able to kill NK-resistant tumor cell lines, autologous and allogeneic fresh tumor targets, and virus-infected cells while remaining substantially non-toxic to normal cells [E. Grimm et al., *J. Exp. Med.*, 144:1823 (1982); S. Rosenberg, *J. Natl. Can. Inst.*, 75:595 (1985)].

A. Adoptive Immunotherapy of Cancer Using LAK Cells and CTL

The use of LAK cells as anti-cancer effectors in combination with recombinant human (rh) IL-2 in adoptive immunotherapy of cancer has resulted in the achievement of temporary remission in a variety of human cancers, especially renal carcinoma and melanoma [S. A. Rosenberg et al., *New Engl. J. Med.*, 313:1485 (1985); S. A. Rosenberg et al., *New Engl. J. Med.*, 316:889 (1987); W. H. West et al., *New Engl. J. Med.*, 316:898 (1987)]. However, LAK cell therapy has had little success against established metastatic disease [Rosenberg et al, (1987), cited above]. Two major problems affect the efficiency of adoptively transferred LAK cells: one is the inadequate tumoricidal activity of these MHC non-restricted polyclonal killer cells; the second is the unavailability of sufficient numbers of activated effectors that retain both cytotoxic and tumor targeting capabilities. The high doses of rh IL-2 administered to the patients to circumvent these limitations have been associated with significant toxicity and adverse side effects [Rosenberg et al., (1985) and Rosenberg et al., (1987), both cited above].

Several alternate approaches have been proposed to improve cancer therapy, including the use of antigen-specific tumor infiltrating cytotoxic lymphocytes (TIL) [Itoh et al, *Cancer Res.*, 46:3011 (1986) and Muul et al, *J. Immunol.*, 138:989 (1987)], the use of LAK cells linked with antibodies to tumor cell surface antigens [Takahashi et al, *Science*, 259:1460 (1993) and Nistico et al, *J. Clin. Invest.*, 90:1093 (1992)], and genetic engineering of tumor cells with cytokine genes (such as IL-2, TNF, IFN-γ, IL-4, IL-6, and IL-7), to promote enhanced anti-tumor immunity [Gansbacher et al, *J. Exp. Med.*, 172:1217 (1990); Gansbacher et al, *Cancer Res.*, 50:7820 (1990); Hock et al, *J. Exp. Med.*, 174:1291 (1991); Golumbeck et al, *Science*, 254:713 (1991); and Asher et al, *J. Immunol.*, 146:3227 (1991)]. In particular, TIL expanded from tumor infiltrates in the presence of high doses of rh IL-2 (6000 U/ml) grow rapidly and become potent cytolytic anti-tumor effectors [Itoh, et al., *Cancer Res.* 46:3011 (1986); Rosenberg, S. A., *Ann. Surg.* 208:121 (1988)]which can be transferred back into the tumor-bearing individuals (together with high doses of IL-2), where they migrate into tumor lesions and promote tumor regression. However, IL-2 therapy in combination with these specific CTL (TIL/IL-2 therapy) has yielded objective tumor regression in only 20–30% of patients with melanoma and carcinoma of the kidney [Rosenberg, et at, *Ann Surg.* 210:474 (1989)]. In addition, high-dose cytokine-related toxicities (including the capillary leak syndrome and renal dysfunction) have precluded extended therapies in many patients [Rosenberg et al, (1987), cited above; Rosenberg, et al, *Ann. Surg.* 210:474 (1989); Lee, et al, *J. Clin. Oncol.* 7:7 (1989); and Lotze, et al. *Hum. Immunol.* 28:198 (1990)].

B. Bone Marrow Purging and Consolidative Immunotherapy (LAK/IL-2 Therapy) in Patients with Leukemia Autologous bone marrow transplantation (ABMT) has shown preliminary promising results both in children with acute myeloblastic leukemia (AML) and acute lymphoblastic leukemia (ALL) in second remission, and in adults with AML in first remission or ALL in second remission [Govin et al, *Bone Marrow Transpl.*, 4:1206 (1989)]. Ex vivo treatment of marrows with pharmacological agents (e.g., 4-hydroperoxycyclophosphamide or 4-HC), or appropriate monoclonal antibodies to remove residual leukemic cells, seems to contribute to the efficacy of these autografts, and marrow purging has been incorporated into several of these studies [Kaizer et al, *Blood*, 77:1534 (1985)]. However, despite the use of these purging procedures, the relapse rate in leukemic patients after ABMT is still almost 50% [Govin et al, (1989), cited above]. Improved marrow purging protocols are, therefore, needed to achieve total eradication of non-detectable malignant blasts in order to prevent disease recurrence.

Within hematologic malignancies, therapy with LAK cells and IL-2 has induced some clinical responses in patients with advanced malignant lymphoma or AML. It is postulated that administration of LAK cells with IL-2 might prevent or delay relapses if used as consolidative immunotherapy against the minimal residual disease (MRD) which exists after ABMT. Although IL-2-responsive LAK precursor cells are in the circulation as early as 3 weeks after ABMT, full LAK activity is recovered only 70–80 days after the transplant. The feasibility of generating and administering autologous LAK cells and IL-2 after ABMT in patients with high risk of relapse is now under investigation. However, this therapeutic modality might have practical limitations in many patients with AML or ALL due to the scarcity of cytotoxic cells in their blood and to the often rapid disease progression.

C. Treatment of Viral Infections with CTL

Dr. P. Greenberg's group (Fred Hutchinson Cancer Research Center, Seattle, Wash.), have been adoptively transferring CTL ($CD3^+CD8^+$) specific for cytomegalovirus (CMV) to reconstitute CMV-specific immunity in immunosuppressed patients [S. A. Riddell et al, In Vitro Cell Devel. Biol., 28:76A (1992)]. Their protocol includes obtaining T cells from the peripheral blood of the patients, expanding them to large quantities in vitro in the presence of virus-infected cells and IL-2, and genetically engineering the specific CTL so generated with a "suicide" gene (herpes virus thymidine kinase). Two problems are inherent to the adoptive immunotherapy protocol with virus-specific CTL clones. First, the cytotoxic cells must be derived from the same patient in which they will be transferred back for treatment. Second, a retroviral mediated gene transfer must be used to introduce in the CTL clones a selectable marker gene and a "suicide" gene to increase the safety of therapy in this setting and eliminate the virus-specific CTL, in case the clones stimulate a life-threatening inflammatory immune response in the patient.

Thus, in the application of adoptive cellular immunotherapy against tumors or against viral-diseases, the therapy by necessity requires obtaining peripheral blood lymphocytes from individual patients, growing them in vitro for an adequate length of time in order to expand a population of IL-2-activated killer cells (LAK or CTL), and reinjecting such cells into the same patient.

There remains a need in the art for convenient, safe, and more effective methods and compositions for the adoptive immunotherapy of cancer and untreatable viral infections, and for purging residual malignant cells remaining after cytoreductive treatments in the bone marrow of patients with leukemia.

SUMMARY OF THE INVENTION

In response to the above-stated need in the art, the present invention provides a clonal, MHC non-restricted and immortal effector cell population able to recognize and attack selectively tumor and virus-infected cells; this effector cell is unique as it represents a universal and powerful reagent for cancer therapy and for treatment of viral diseases.

In one aspect of this invention, a method for modifying an established (immortal) cell line, designated TALL-104, which displays potent MHC non-restricted cytotoxicity against a broad spectrum of tumor cells and virus-infected cells, without damaging or killing cells from normal tissues, is disclosed. This method modifies the TALL-104 cells to confer one or more desired characteristics that will make the cells suitable for use in marrow purging and in adoptive transfer immunotherapy in allogeneic (HLA-mismatched) recipients. This method includes the steps of maximizing the cytotoxicity of the TALL-104 cell line by a short treatment (18 hours) in vitro with a selected cytokine, e.g., IL-2 alone or combined with IL-12, followed by γ-irradiating the activated cells to arrest irreversibly their proliferation.

As another aspect, the invention provides the modified TALL-104 cell line prepared by the above-described method.

As a further aspect, the invention provides a method for killing tumor cells (or virus-infected cells) in vivo. The method involves administering to a patient, e.g., a immunosuppressed recipient, the modified cytotoxic TALL-104 cell line described above. The modified cell line is preferably administered by i.v. injection in a suitable carrier, such as saline.

As still a further aspect, the invention provides a method for killing malignancies in animals, particularly domestic animals such as dogs and cats, respectively. The method involves administering to an immunosuppressed animal the modified cytotoxic TALL-104 cell line described above, preferably by i.v. injection in a suitable carrier, such as saline.

In yet another aspect, the invention provides a method for eliminating residual tumor cells from patients' bone marrow (marrow purging) by ex vivo treatment of such marrow with the modified cytotoxic TALL-104 cell line followed by autologous bone marrow transplant (ABMT) and by consolidative immunotherapy with the modified TALL-104 cells.

Other aspects and advantages of the present invention are discussed further in the following detailed description of the preferred embodiments thereof.

BRIEF DESCRIPTION OF THE DRAWINGS

FIG. 1A is a bar graph demonstrating the cytotoxic activity (expressed as 40% lytic units (LU)) of IL-2 activated TALL-104 cells against HIV chronically infected (U-1) and uninfected (U937) myelomonocytic leukemia. Phorbol myristate acetate (PMA) was given to the targets 24 and 48 hours before the cytotoxic assay to induce virus production.

FIG. 1B is a bar graph demonstrating the cytotoxic activity of IL-2 activated TALL-104 cells against HIV chronically infected ($AcH_2$) and uninfected (CEM) T lymphocytic leukemia. Treatment of targets with PMA for 24 and 48 hours increased viral production and sensitivity to lysis by TALL-104 cells.

DETAILED DESCRIPTION OF THE INVENTION

Figure 2A:
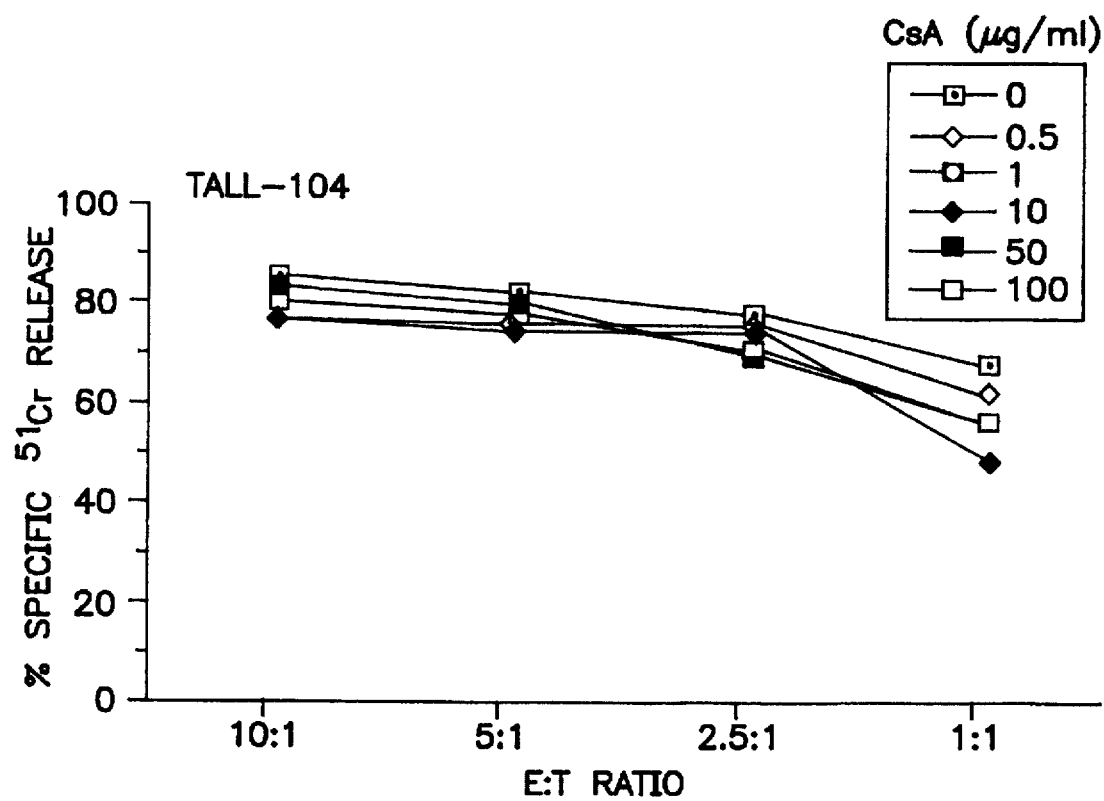
FIG. 2A is a graph illustrating the dose-dependent effects of cyclosporin A (CsA) on the cytotoxicity ($^{51}Cr$ release) of IL-2 activated TALL-104 cells.

The present invention meets the above-mentioned need in the art by providing a method for modifying a highly cytotoxic T cell line (TALL-104) established from a child with T lineage acute lymphoblastic leukemia and, the modified TALL-104 cell line as therapeutic reagents. The TALL-104 cell, line is immortal (i.e., can be maintained indefinitely in vitro). The unmodified cell line is believed to be the first immortal human cell line having such a broad and extremely high antiviral and antitumor cytotoxic activity in vitro and in vivo, as described below. The growth of these modified cells can be arrested when used in vivo for adoptive transfer therapy, and the modified cells would not be rejected by immunosuppressed HLA-mismatched recipients. In addition, these non-proliferating cells maintain a high migratory ability in the tissues of the immunosuppressed recipient, thus being able to interact with and kill tumor and virus-infected targets.

A. The Unmodified TALL-104 Cell Line

The isolation, characterization, and maintenance of unmodified TALL-104 cells are described in detail in Examples 1 and 2 [see, also, O'Connor et al., *Blood*, 77:1534–1545 (1991), which is incorporated by reference herein]. See, also, U.S. Pat. No. 5,272,082, issued Dec. 21, 1993.

The unmodified TALL-104 cell line is permanently established in tissue culture and has been continuously maintained in vitro since 1990. The cell line is kept within the laboratory of Dr. Daniela Santoli at The Wistar Institute of Anatomy and Biology, Philadelphia, Pa., and has been deposited with American Type Culture Collection (ATCC) as ATCC Accession No. CRL 11386.

The unmodified TALL-104 T cell line of this invention, designated TALL-104, has a CD3$^+$/TCRαβ$^+$, CD4$^-$, CD8$^+$, CD56$^+$, CD16$^-$ phenotype, as defined by immunofluorescence analysis with a panel of monoclonal antibodies and compared to the phenotype of purified Natural Killer (NK) cells and lymphokine-activated killer (LAK) cells (see Table I below).

TABLE I

| Surface markers | TALL-104 | LAK | NK |
| --- | --- | --- | --- |
| CD2 | 39–45* | 79–94 | 80–90 |
| CD3 | 98–100 | 78–95 | <1 |
| TCR-αβ | 98 | 45–53 | <1 |
| CD4 | <1 | 44–62 | <1 |
| CD8 | 91–96 | 37–55 | 60–80 |
| CD16 | <1 | 10–20 | 99 |
| CD56 | 94 | 9–17 | 99 |

*Percent positive cells, as determined by immunofluorescence analysis.

These surface markers indicate that TALL-104 cells have a phenotype compatible with a clonal cytotoxic T cell subset. The lack of surface expression of CD16, a classical surface marker of NK cells, and the presence of a T cell receptor (TCR) with the α/β heterodimer, both indicate that these cells belong to the T cell lineage and not to the NK cell lineage. By contrast, the antigenic profile of IL-2-expanded LAK cells, as shown above, indicates the heterogeneity of the LAK cell population which includes activated NK and T cells.

This TALL cell line recognizes the same tumor targets as conventional LAK cells but, being clonal, it is much more potent. In fact, after modification as described herein in part B below, (e.g., after lethal irradiation (4000 rads) using a Cesium source) the TALL-104 cells, but not LAK cells, remain highly cytotoxic. This phenomenon is the opposite of the one that has been reported in the literature with primary cytotoxic leukemic T cell cultures, where irradiation abrogated completely their cytotoxic activity in response to IL-2 [Kaufmann et al. *J. Immunol.* 139:977–982, (1987)].

The TALL-104 cell line has a characteristic chromosomal translocation involving chromosomes 11 and 14, i.e., at t(11;14) (p13:q11). TALL-104 cell line is further characterized by TCR rearrangements alpha, beta, gamma and delta, and the ability to produce lymphokines such as GM-CSF, IFN-gamma, TNF-α, and TGF-β1.

The TALL-104 cell line is extremely cytotoxic against a broad spectrum of tumor cells and of virus-infected cells. Specifically, the cell line displays potent MHC non-restricted cytotoxicity against a broad variety of tumor cells (including human leukemias and solid tumors) (Tables II and III) and virus-infected cells (Table IV and FIGS. 1A and 1B), without damaging or killing cells from normal tissues. Tables II and III also show that conventional NK and LAK cells display a lower cytotoxic efficiency and a more restricted spectrum of activity against tumor and virus-infected targets, as compared to the TALL-104 cell line.

Importantly, as shown in Table II below, the TALL-104 cell line is completely resistant to lysis by allogeneic NK and LAK cells and CTL, and thus would not be destroyed by the immune system of HLA-mismatched recipients. Cytotoxic activity was measured as described in Cesano and Santoli, *In Vitro Cell Dev. Biol.*, 28A:648–656 (1992).

TABLE II

Cytotoxic efficiency of TALL-104 cells as compared to normal NK and LAK cells against leukemic targets

| | Effectors | | |
|---|---|---|---|
| Leukemic target | NK[a] | LAK[b] | TALL-104[c] |
| Cell Lines | | | |
| K562 (CML) | 2125 ± 1125[d] | 7125 ± 871 | 7831 ± 112 |
| U937 (myelomonocytic) | 2373 ± 915 | 6908 ± 1002 | 7183 ± 82 |
| THP-1 (monocytic) | <1 | 2113 ± 307 | 2983 ± 112 |
| HL60 (promyelocytic) | 308 ± 115 | 4168 ± 605 | 5999 ± 99 |
| Raji (B-lymphoma) | <1 | 1160 ± 302 | 3890 ± 201 |
| Daudi (B-lymphoma) | 102 ± 13 | 3987 ± 731 | 7999 ± 81 |
| ALL-1 (Pre-B ALL) | <1 | 113 ± 32 | 1983 |
| ALL-2 (Pre-B ALL) | <1 | 83 ± 31 | 2001 |
| ALL-3 (Pre-B ALL) | <1 | 201 ± 83 | 1876 |
| TALL-101 (T-ALL) | <1 | 1152 ± 102 | 2931 |
| TALL-103/2 (T-ALL) | <1 | 820 ± 98 | 3783 |
| TALL-103/3 (T-ALL) | 280 ± 80 | 1476 ± 123 | 5676 |
| TALL-104 (T-ALL) | <1 | <1 | <1 |
| TALL-105 (T-ALL) | < | 360 ± 56 | 1176 |
| TALL-106 (T-ALL) | < | 1120 ± 132 | 4987 |
| Primary leukemic samples | | | |
| AML (FAB-M5) | <1 | <1 | 3183 |
| T-ALL | <1 | <1 | 1183 |
| Normal bone marrows | | | |
| Donor A | <1 | <1 | <1 |
| Donor B | <1 | <1 | <1 |
| Donor C | <1 | <1 | <1 |

[a]Freshly isolated PBL from healthy donors.
[b]PBL from healthy donors incubated in rh IL-2 (100 U/ml) for 3 days.
[c]TALL-104 cells maintained in rh IL-2 (100 U/ml).
[d]40% LU/$10^8$ cells.
[e]Not determined.

TABLE III

Cytotoxic efficiency of TALL-104 cells as compared to normal NK and LAK cells against cell lines derived from solid tumors

| | Effectors | | |
|---|---|---|---|
| Solid tumor target | NK[a] | LAK[b] | TALL-104[c] |
| Glioblastoma | | | |
| U373-MG | <1[d] | 2777 ± 1326 | 4186 |
| U87-MG | <1 | 4183 ± 493 | 8706 ± 210 |
| WA2323-2 | <1 | 1008 ± 375 | 4121 |
| Neuroblastoma | | | |
| CHP-100 | n.d.[e] | 860 | 3383 |
| CHP-134 | n.d. | 998 | 1943 |
| Melanoma | | | |
| FO-1 | 429 ± 171 | 2073 ± 27 | 7108 |
| FO-1 (HLA⁻ variant) | 775 ± 550 | 2680 ± 385 | 7992 |
| SK-MEL-33 | 388 ± 15 | 1700 ± 101 | 6899 |
| SK-MEL-33 (HLA⁻ variant) | 667 ± 480 | 1916 ± 290 | 8193 |
| WM-451 | <1 | 2633 ± 789 | 3158 |
| WM-1985 | <1 | 2083 ± 535 | 4165 |
| WM-793 | <1 | 1924 ± 549 | 8291 |
| WM-852 | <1 | 2151 ± 347 | 8970 |
| Bladder carcinoma | | | |
| 5637 | <1 | 5086 ± 240 | 6177 |
| Ovarian carcinoma | | | |
| OVCA3 | <1 | n.d. | 4848 |
| 2774 | <1 | n.d. | 2177 ± 83 |
| NIH-OVCA3 | | | 3269 |
| Breast carcinoma | | | |
| H$_s$568-T | n.d. | n.d. | 6522 ± 121 |
| MDA-MD468 | n.d. | n.d. | 7198 |
| Prostate carcinoma | | | |
| PC-3 | n.d. | n.d. | 5382 |
| DU-145 | n.d. | n.d. | 8893 |
| Ln CHP | n.d. | n.d. | 2144 |
| Lung carcinoma | | | |
| A459 | <1 | 212 ± 143 | 1598 ± 113 |
| CaLu-1 | <1 | 316 ± 215 | 2264 |
| CaLu-6 | <1 | 161 ± 23 | 1239 |

[a]Freshly isolated PBL from healthy donors.
[b]PBL from healthy donors incubated in rh IL-2 (100 U/ml) for 3 days.
[c]TALL-104 cells maintained in rh IL-2 (100 U/ml).
[d]40% LU/$10^8$ cells.
[e]Not determined.

Further, as illustrated in Table IV below, the cytotoxic activity of the TALL-104 cell line against virus-infected cells is also higher than that of NK and LAK cells from healthy donors measured as described in Santoli et al, *J. Immunol.*, 121:526–531 (1978) and *J. Immunol.*, 121:532–538 (1978), incorporated by reference herein. The results are expressed in 40% lytic units (LU)/$10^8$ cells. Interestingly, at the effector-target (E/T) ratio of 50:1, HIV-infected CEM and U937 cells were killed as efficiently as the uninfected counterpart by purified NK cells (Table IV). In contrast, at the E/T ratio of 10:1, TALL-104 cells killed more efficiently the HIV infected targets than the uninfected ones. These in vitro results indicate the ability of the TALL effectors to lyse efficiently virus-infected targets and the utility of the TALL cells in the treatment of lethal viral diseases in vivo.

It is also anticipated that when modified as described in part B (i.e., lethally irradiated and cytokine activated) TALL-104 cells can be employed to treat non-human primates (cynomologous monkeys) infected with simian immunodeficiency virus (SIV), which is the equivalent of HIV. This is done by administering the modified TALL-104 cells into immunosuppressed monkeys at various stages of SIV infection. Such studies permit evaluation of the possible toxicity of TALL-104 cells in primates. If toxicity develops due to release by TALL-104 cells of high levels of toxic mediators, such as TNF-α, TNF receptors may be eliminated from the TALL-104 cells by conventional methods, such as the construction of deletion mutants (see U. S. Pat. No. 5,272,082, issued Dec. 21, 1993). Such evaluation permits the development of safe, non-toxic protocols of adoptive transfer therapy in humans and animals.

TABLE IV

Cytotoxic efficiency of γ-irradiated TALL-104 cells against virus-infected cells

| Target | Virus | NK | LAK | TALL-104 |
|---|---|---|---|---|
| FS-5 (fibroblasts) | none | <1 | 110 | 299 |
|  | CMV | 810 | 2683 | 10,183 |
| CHP-134 | none | ND | ND | 1043 |
| (neuroblastoma) | PR8 | ND | ND | 7407 |
| CEM (leukemic | none | 111 | 1483 | 1692 |
| T cell line) | HIV | 155 | 1603 | 6327 |
| U937 (leukemic | none | 746 | 1382 | 4462 |
| myeloid cell line) | HIV | 697 | 2129 | 8737 |

CMV = cytomegalovirus
PR8 = influenza virus
HIV = human immunodeficiency virus
ND = not determined The cytotoxic properties of the TALL-104 cell line are described in more detail in Cesano and Santoli, *In Vitro Cell Dev. Biol.* 28A:648 (1992); and Cesano, et al, *J. Immunol.*, 151:2943 (1993). The above references are incorporated by reference herein for this non-essential disclosure.

The cell line of this invention is further characterized by being free of any contaminating virus, including Epstein-Barr virus (EBV) and retroviruses such as HTLV-1, HTLV-II, and HIV, as tested by electronmicroscopy, reverse transcriptase assays and Southern blot analysis using specific viral DNA probes.

The TALL-104 cell line offers the advantage over conventional LAK and NK cells from healthy donors and primary leukemic T cell cultures of being immortal, i.e., permanently and rapidly growing in vitro in the presence of rhIL-2, and thus providing unlimited material for in vitro and in vivo studies. Another advantage of these cells is that they are clonal populations, thus phenotypically and functionally stable thereby eliminating the intervariability and reproducibility problems encountered with LAK cells from different donors which represent heterogenous cell populations.

Figure 2B:
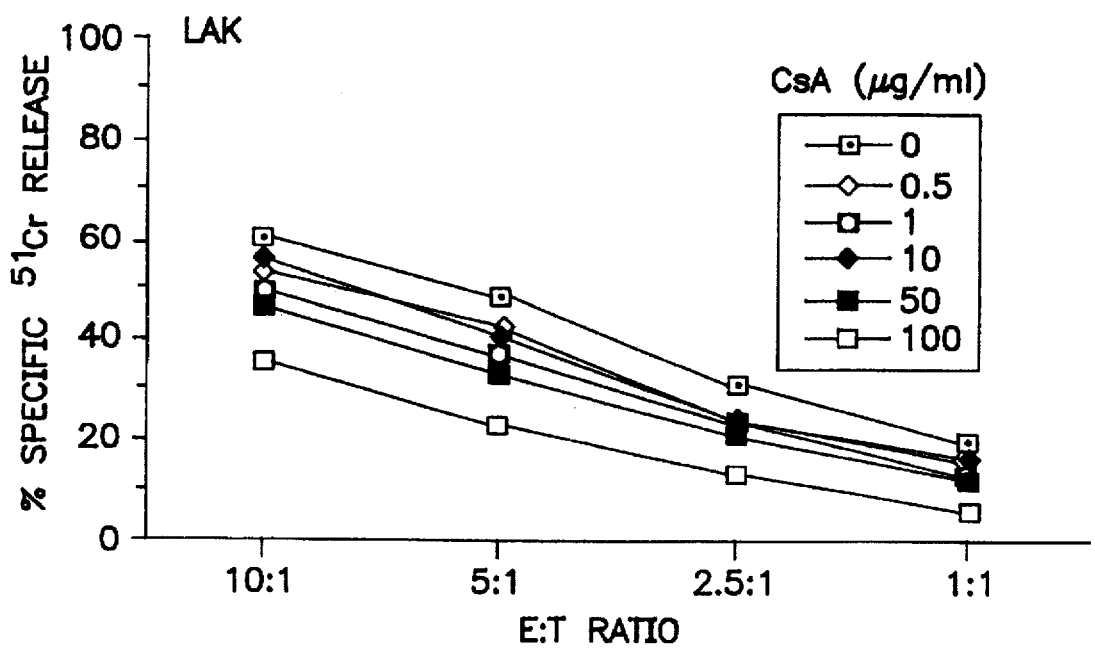
FIG. 2B is a graph illustrating the dose-dependent effects of cyclosporin A (CsA) on the cytotoxicity ($^{51}Cr$ release) of IL-2 activated LAK cells.
Figure 2C:
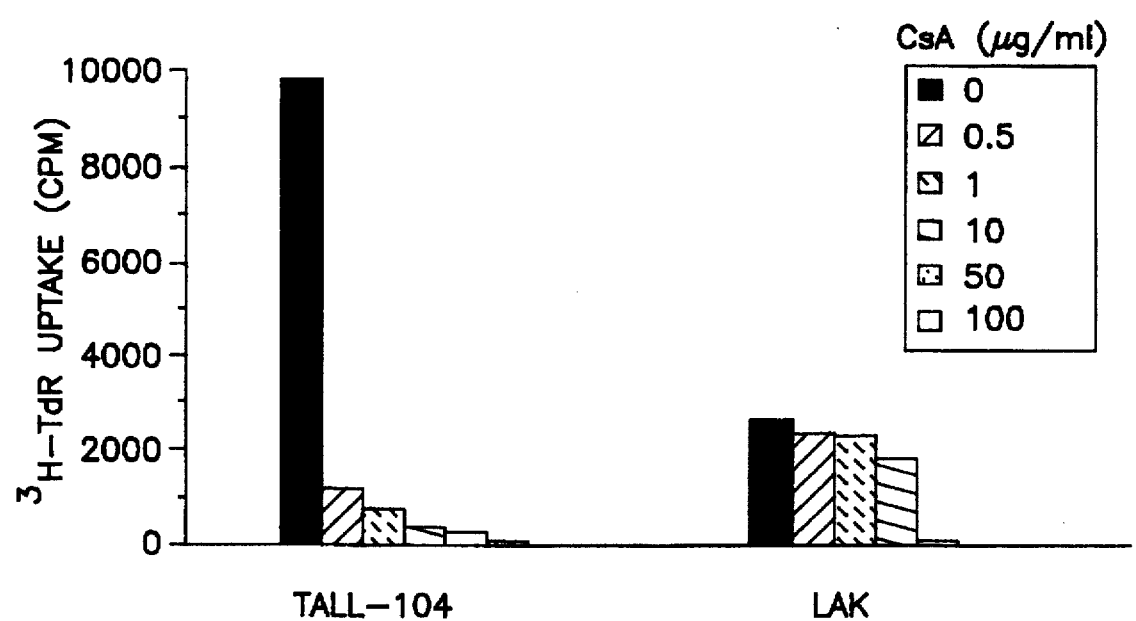
FIG. 2C is a bar graph illustrating the dose-dependent effects of CsA on the proliferation ($^3H$-TdR uptake) of IL-2 activated TALL-104 cells and LAK cells. The effectors were treated for 18 hours with CsA before being tested for [$^3H$]TdR uptake and cytotoxic activity against Raji cells (an NK-resistant target). Results of one representative experiment are shown; similar data were obtained with LAK cells from three donors and with TALL-104 cells in three more experiments.

A further advantage of the TALL-104 cell line is that it retains cytotoxic activity even in the presence of immunosuppressive drugs, e.g., the drugs used in organ transplantation like Cyclosporin A (CsA) that block the immune response of the host. As shown in FIG. 2A to 2C even when used at doses 3 logs higher than the therapeutic levels reached in the patients blood (e.g. 100 μg/ml), CsA does not impair the cytotoxic activity of the TALL-104 cells. In contrast, CsA impairs the cytotoxicity of LAK cells (FIGS. 2A to 2C).

Based on the unique behavior of TALL-104 cells in the presence of a suitable immunosuppressive drug, such as CsA, these cells can be injected in MHC mismatched immunosuppressed recipients, and still exert their cytotoxic activity without being rejected. It is anticipated that these cells will display the same activity when administered with, or exposed to, other immunosuppressive drugs routinely used in clinical practice (e.g., glucocorticoids).

Unmodified TALL-104 cells can grow in vivo in severe combined immunodeficient (SCID) mice infiltrating their tissues [Cesano et al. *Blood*, 77:2463–2474 (1991)]. These cells do not compartmentalize in specific tissues but rather can reach every tissue in the organism depending on the route of administration. Because the cell line might be leukemogenic if injected into an immunosuppressed host, it must be modified to control or arrest cell growth without affecting its killer function.

B. Modified TALL-104 Cell Line

The modification of TALL-104 cells according to the invention and as described in detail below involves both cytokine potentiation of the lytic function and growth arrest by lethal irradiation. Such modification makes the cells suitable (effective and safe) for use in marrow purging to achieve complete eradication of residual malignant blasts in patients with leukemia and other types of cancer and in adoptive cellular immunotherapy of cancer and untreatable viral diseases in allogeneic (MHC-mismatched) patients.

According to this invention, the TALL-104 cells are modified to permit them to display an increased cytotoxicity against tumor and virus-infected targets. One modification step includes in vitro treatment of the TALL-104 cells with a selected cytokine or combination of cytokines. For example, the two interleukins, rhIL-2 and rhIL-12, when used independently to treat the cell line, induce the cell line s cytotoxic activity. When these cytokines are used together to modify the cell line, the modified cell line displays additive or increased cytotoxic effects. This results in a significant increase in cytotoxic activity and recycling capability, ultimately leading to 100% elimination of tumor targets at an E:T ratio <0.1:1 [Cesano et al, *J. Immunol.*, 151:2943 (1993)].

Another modification step of this invention involves the exposure of the TALL-104 cell line to lethal irradiation to confer irreversible loss of growth capability with full retention of cytotoxic activity, both in vitro and in vivo. This is achieved by subjecting the cell lines to γ-irradiation just prior to their use. Preferably, the cells are irradiated at 4000 rads using a $^{137}$Cs source. The cells may be irradiated for about 30 minutes to achieve this effect.

Figure 3:
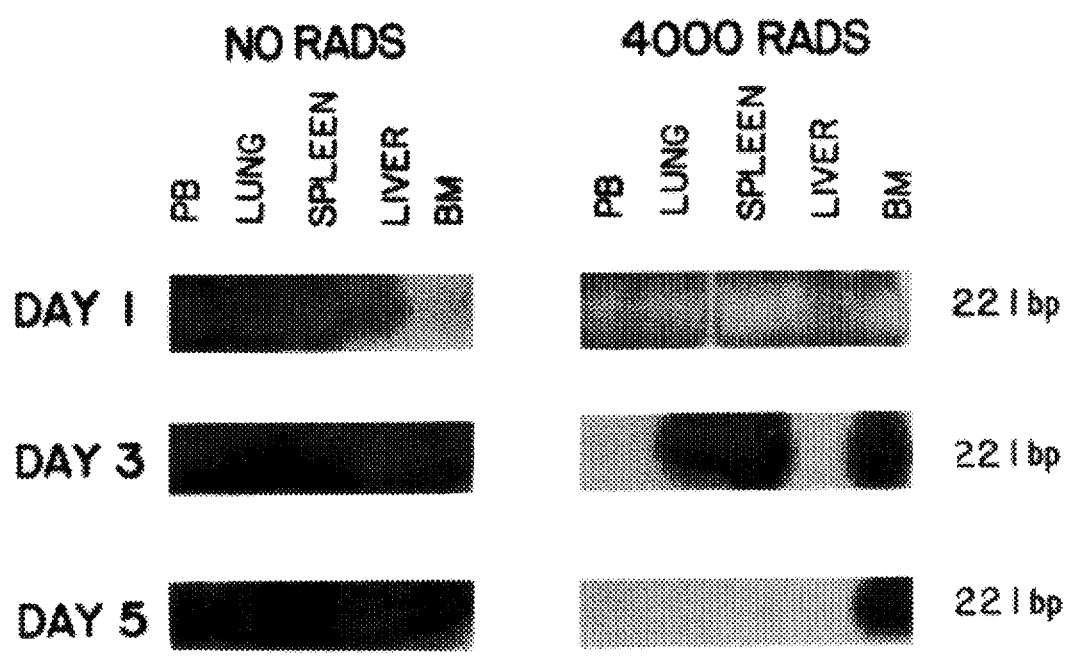
FIG. 3 illustrates the comparative biodistribution of irradiated (i.e., modified) and non-irradiated TALL-104 cells in SCID mouse tissues. Detection of the intraperitoneally (i.p.) implanted TALL-104 cells was done by PCR using human ALU-DNA sequences.
Figure 4A:
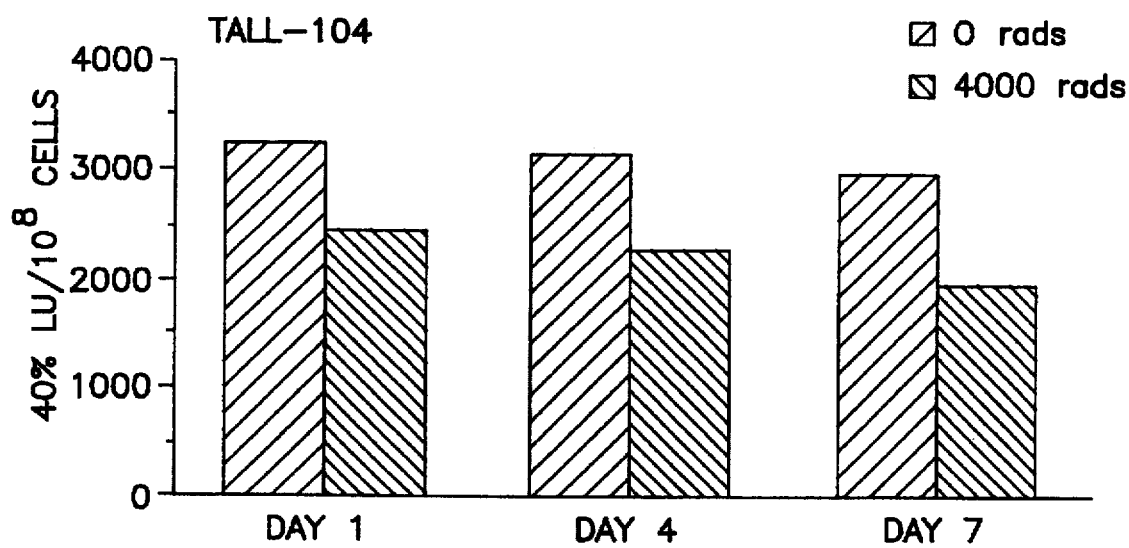
FIG. 4A is a bar graph illustrating the long-term effects of γ-irradiation (4000 rads) on the cytotoxic efficiency of TALL-104 cells. The effectors were tested for ability to lyse $^{51}$Cr-labeled Raji cells on days 1, 4, and 7 after γ-irradiation; IL-2 (100 U/ml) was added to the effectors the day before each cytotoxic assay in order to booster their lytic activity. Results are expressed as 40% LU. The same cells were tested for [$^3$H]TdR uptake. Results are representative of one experiment out of three performed with different LAK donors with similar results.
Figure 4B:
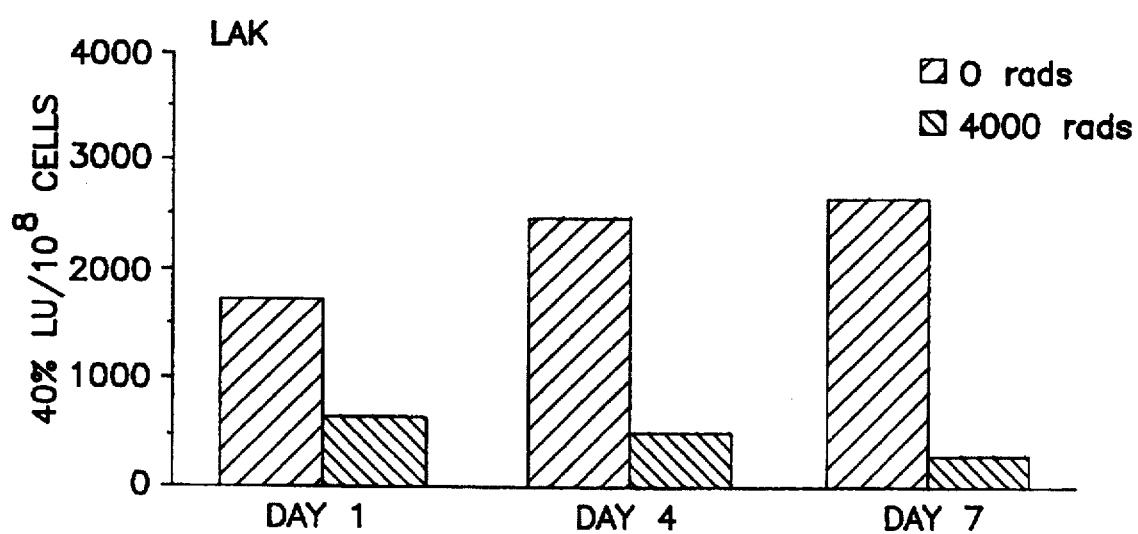
FIG. 4B is a bar graph illustrating the long-term effects of γ-irradiation (4000 rads) on the cytotoxic efficiency of LAK cells. The effectors were tested and results obtained as described for FIG. 4A.
Figure 4C:
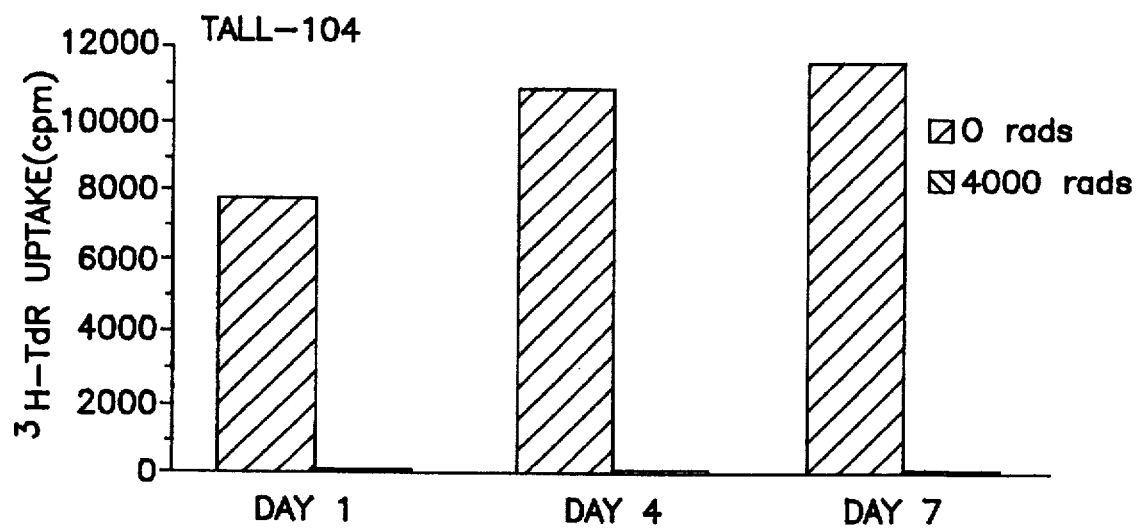
FIG. 4C is a bar graph illustrating the long-term effects of γ-irradiation (4000 rads) on the proliferation of TALL-104 cells. The effectors were tested and results obtained as described for FIG. 4A.
Figure 4D:
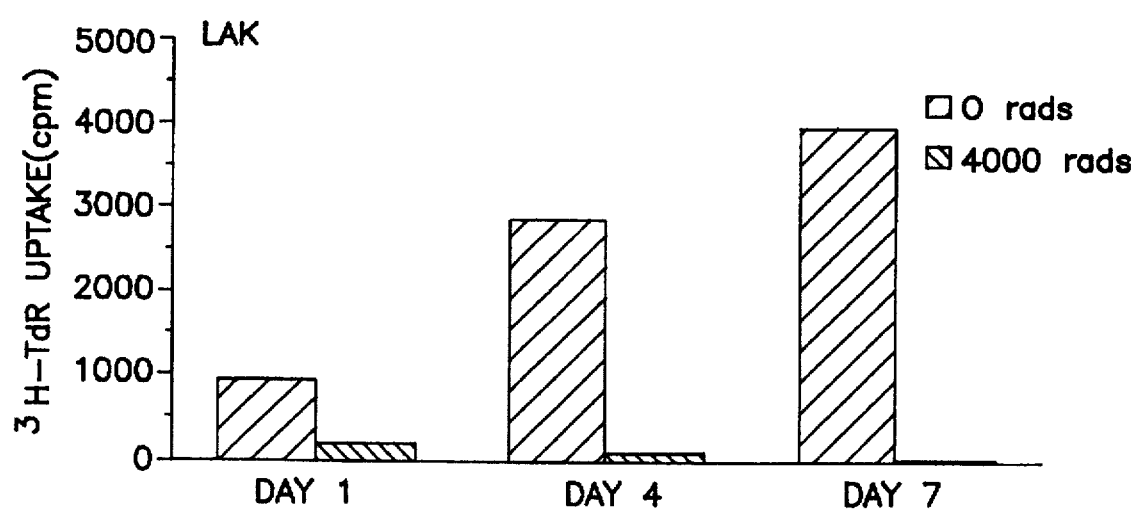
FIG. 4D is a bar graph illustrating the long-term effects of γ-irradiation (4000 rads) on the proliferation of LAK cells. The effectors were tested and results obtained as described for FIG. 4A.
Figure 5A:
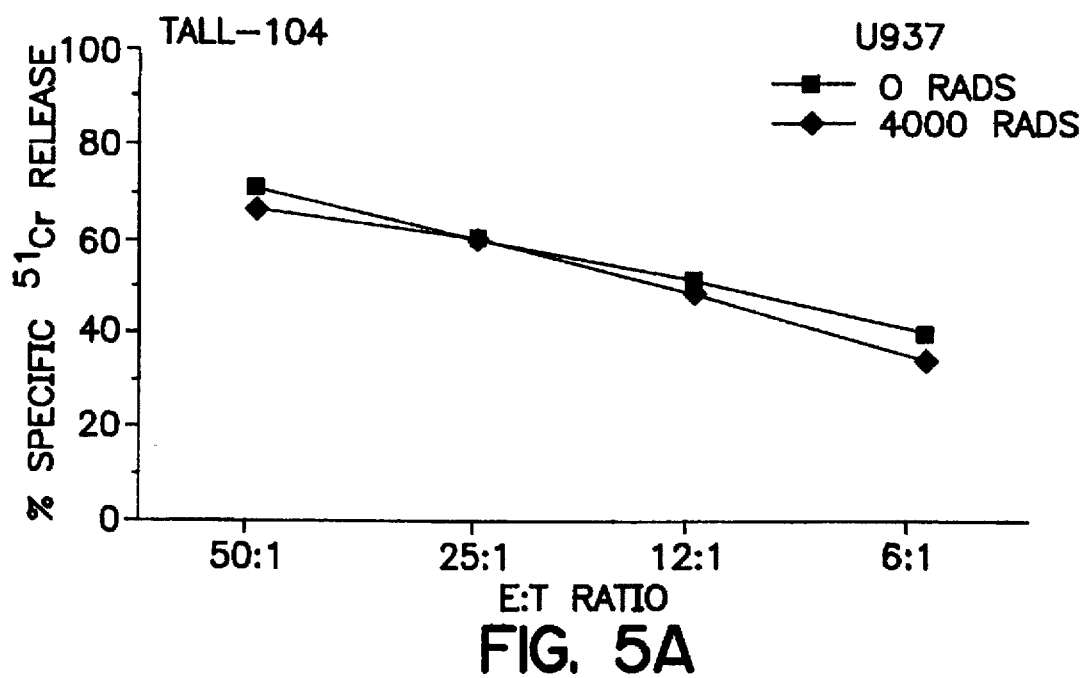
FIG. 5A is a graph illustrating the short-term effects of γ-irradiation (4000 rads) on the tumoricidal activity of TALL-104 cells. The effectors were tested immediately after irradiation against the U937 myelomonocytic leukemia tumor cell line in a 4 hour $^{51}$Cr-release assay, as compared to non-irradiated effectors. Mean±SD values for LAK cells were calculated from three experiments in which three different LAK donors were used. No SD were observed in the case of modified or unmodified TALL-104 cells in several cytotoxic assays.
Figure 5B:
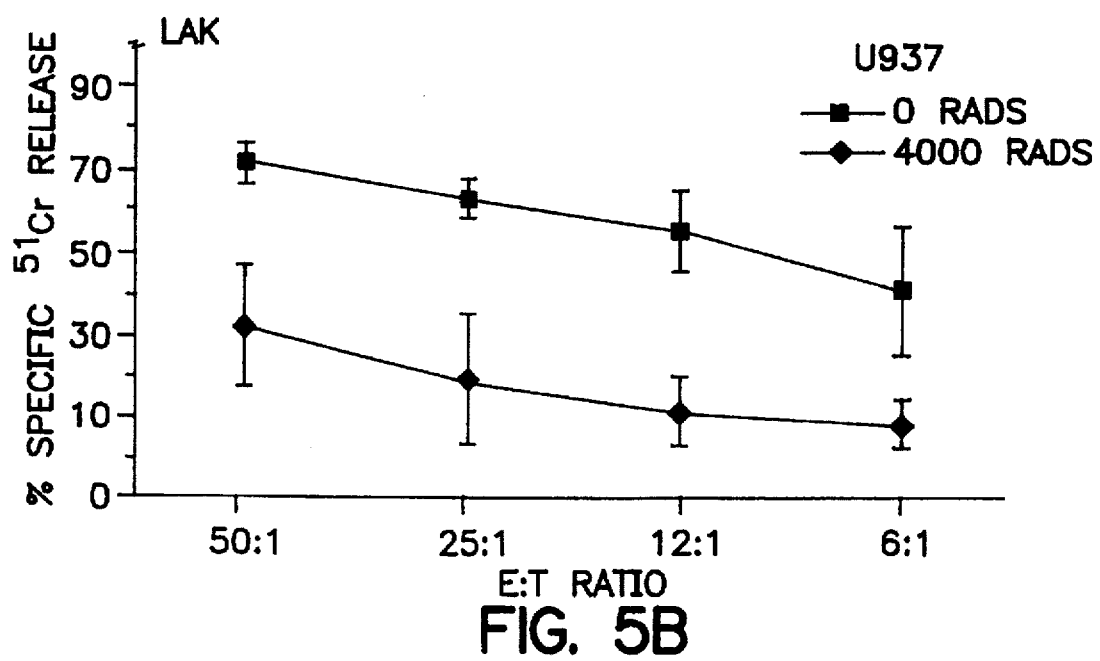
FIG. 5B is a graph illustrating the short-term effects of γ-irradiation (4000 rads) on the tumoricidal activity of LAK cells. The effectors were tested immediately after irradiation against the U937 myelomonocytic leukemia tumor cell line in a 4 hour $^{51}$Cr-release assay, as compared to non-irradiated effectors. Mean±SD values were calculated as described in FIG. 5A.
Figure 5C:
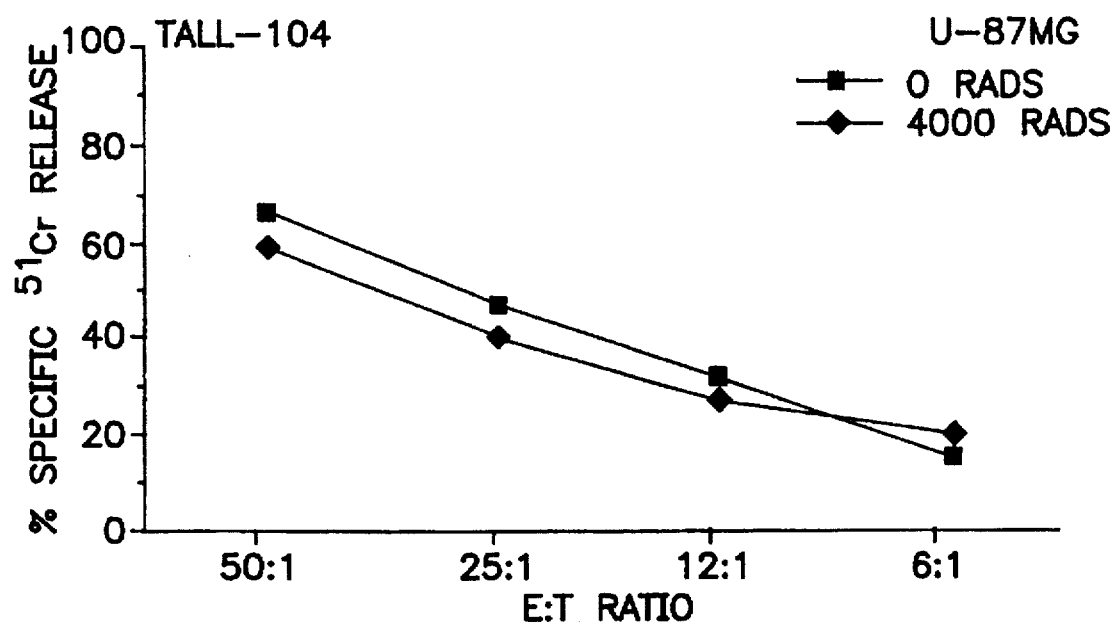
FIG. 5C is a graph illustrating the short-term effects of γ-irradiation (4000 rads) on the tumoricidal activity of TALL-104 cells. The effectors were tested immediately after irradiation against the U-87MG glioblastoma tumor cell line in a 4 hour $^{51}$Cr-release assay, as compared to non-irradiated effectors. Mean±SD values were calculated as described in FIG. 5A.
Figure 5D:
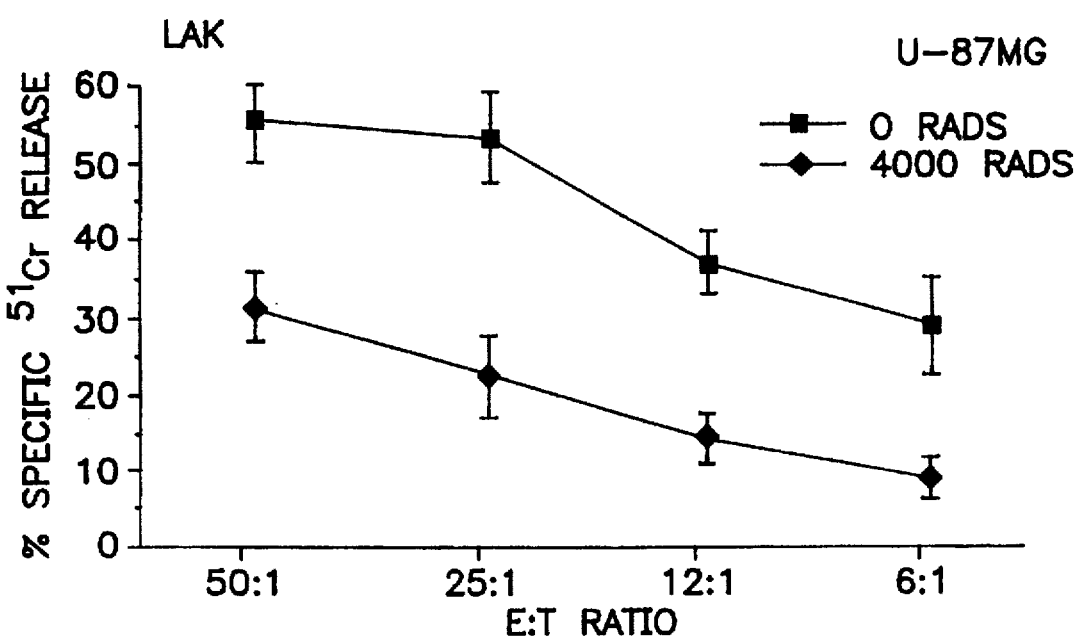
FIG. 5D is a graph illustrating the short-term effects of γ-irradiation (4000 rads) on the tumoricidal activity of LAK cells. The effectors were tested immediately after irradiation against the U-87MG glioblastoma tumor cell line in a 4 hour $^{51}$Cr-release assay, as compared to non-irradiated effectors. Mean±SD values were calculated as described in FIG. 5A.
Figure 5E:
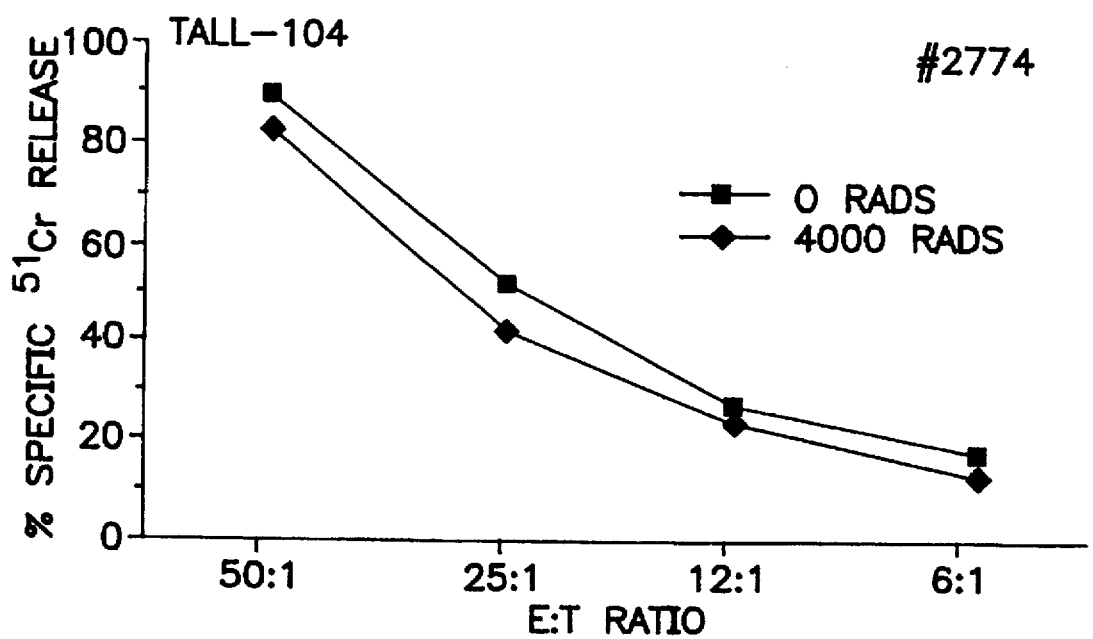
FIG. 5E is a graph illustrating the short-term effects of γ-irradiation (4000 rads) on the tumoricidal activity of TALL-104 cells. The effectors were tested immediately after irradiation against the 2774 ovarian carcinoma tumor cell line in a 4 hour $^{51}$Cr-release assay, as compared to non-irradiated effectors. Mean±SD values were calculated as described in FIG. 5A.
Figure 5F:
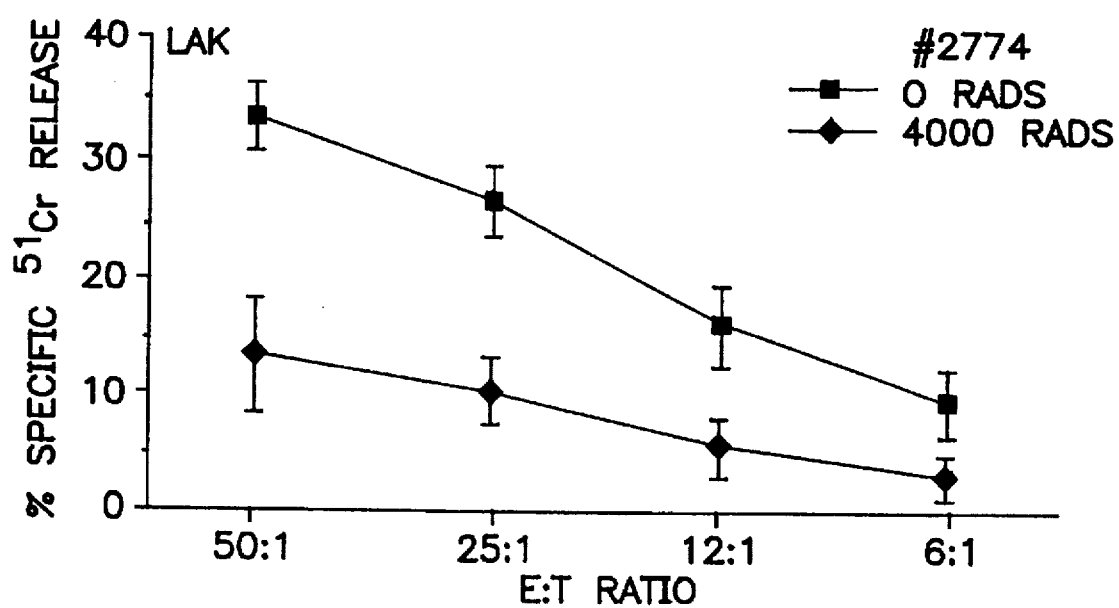
FIG. 5F is a graph illustrating the short-term effects of γ-irradiation (4000 rads) on the tumoricidal activity of LAK cells. The effectors were tested immediately after irradiation against the 2774 ovarian carcinoma tumor cell line in a 4 hour $^{51}$Cr-release assay, as compared to non-irradiated effectors. Mean±SD values were calculated as described in FIG. 5A.
Figure 6:
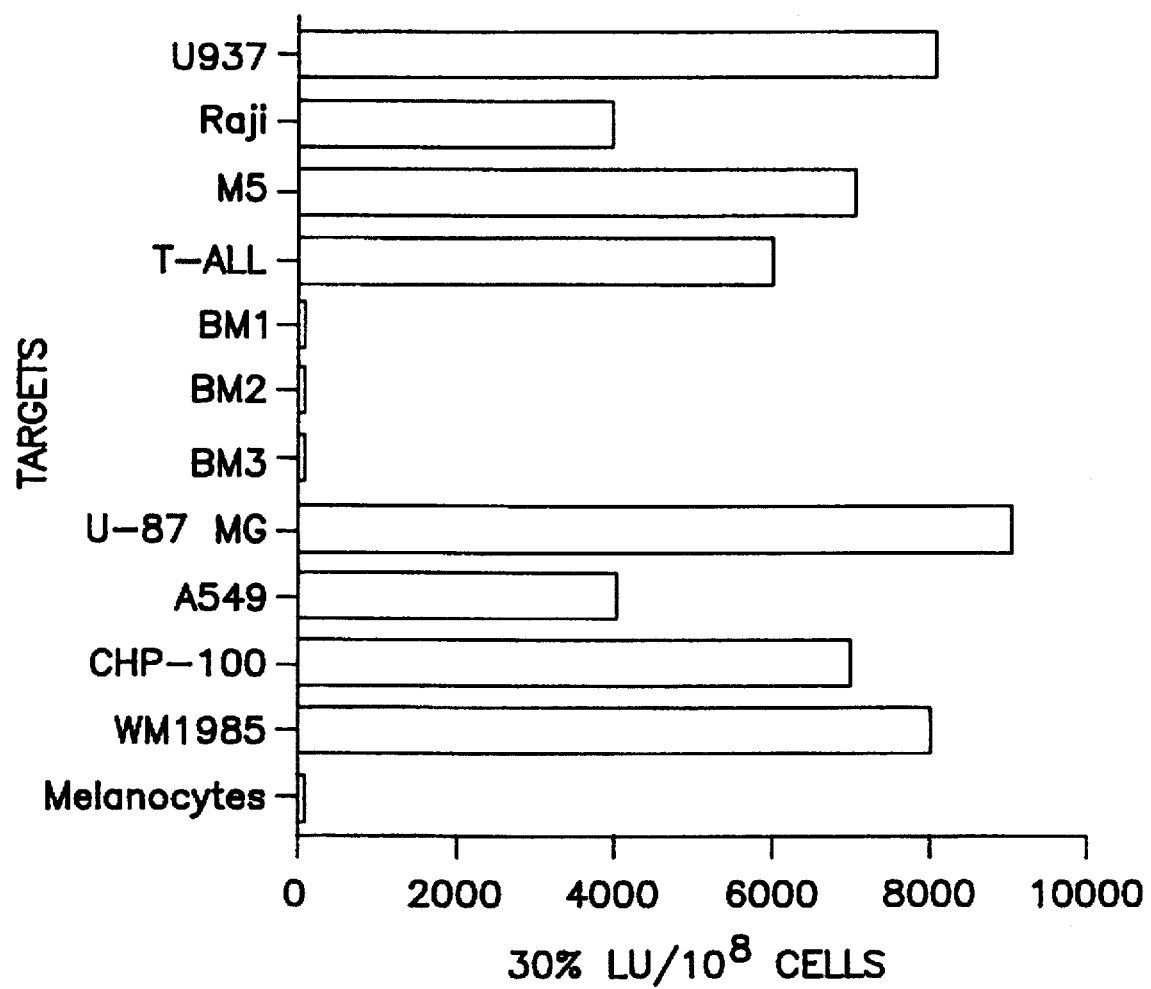
FIG. 6 is a bar graph illustrating the ability of γ-irradiated (modified) and unmodified TALL-104 cells to selectively kill tumor targets and not normal cells. $^{51}$Cr-labeled tumor targets (see Table III and IV), normal bone marrow (BM) cells (BM1-BM3) and normal melanocytes, all listed in the ordinate were tested ($10^4$/well) for susceptibility to lysis by modified TALL-104 cells at four different concentrations. The results of the 4 hour cytotoxic assay were expressed as 30% LU/$10^8$ effectors.
Figure 7A:
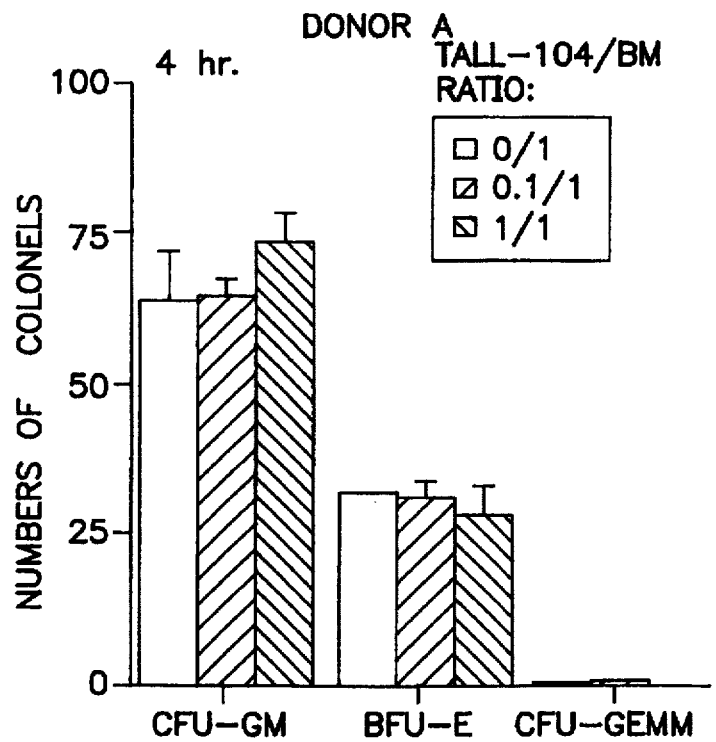
FIG. 7A is a bar graph illustrating the lack of toxicity of γ-irradiated (modified) TALL-104 cells against bone marrow precursors, as determined by their capacity to form colonies in methylcellulose. Modified TALL-104 cells were mixed with BM cells from Donor A for 4 hours at the indicated ratios. The cell mixtures were subjected to a clonogenic assay and the colonies (CFU or BFU) counted after 14 days.
Figure 7B:
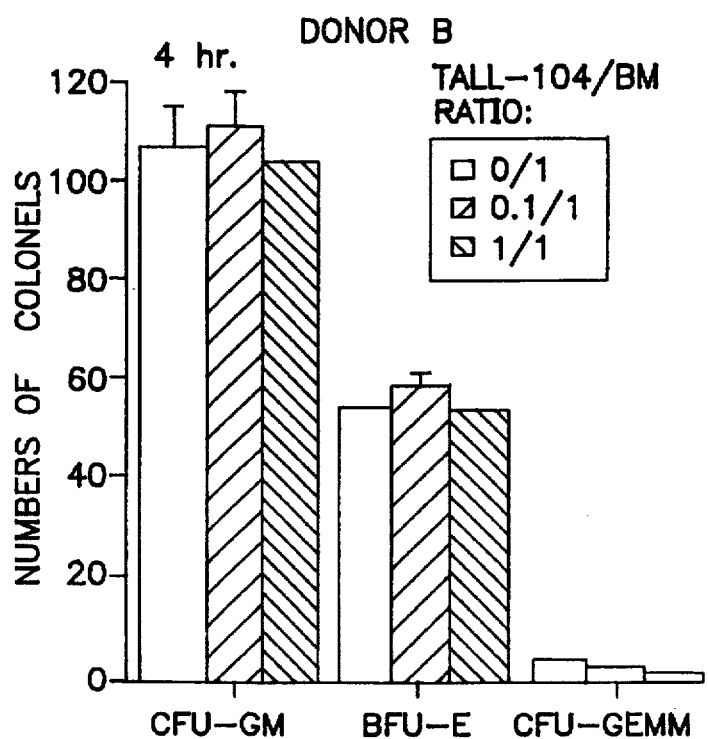
FIG. 7B is a bar graph illustrating the results of the process described for FIG. 7A, but using BM cells from a second Donor B.
Figure 7C:
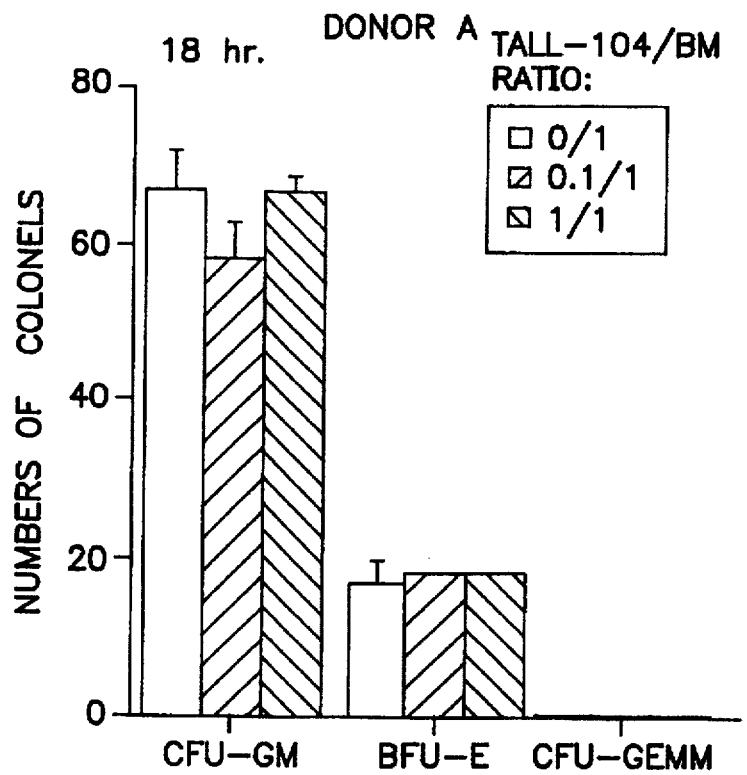
FIG. 7C is a bar graph illustrating the results of the process described for FIG. 7A, except that the BM and TALL-104 cells were mixed for 18 hours.
Figure 7D:
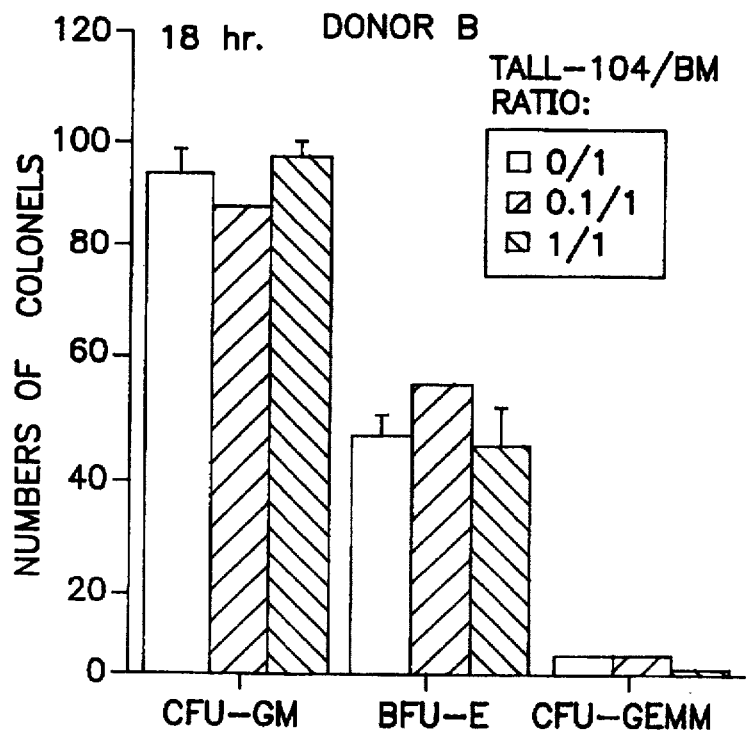
FIG. 7D is a bar graph illustrating the results of the process described for FIG. 7C, but using BM cells from a second Donor B.

The modified, lethally irradiated TALL-104 cells are no longer leukemogenic in SCID mice, confirming the gradual loss of viability observed in vitro. The biodistribution and length of survival of the irradiated cells in SCID mouse tissue were investigated by injecting $10^7$ TALL-104 cells i.p. into the animals, and by performing PCR analysis with primers specific to human ALU-DNA sequences on various organs and at different intervals. FIG. 3 compares the kinetics of biodistribution of modified (irradiated) and unmodified (non-irradiated) TALL-104 cells in the PB, BM, spleen, lung, and liver in mice sacrificed on days 1, 3, and 5 after transfer. On day 1, both modified (irradiated) and unmodified (non-irradiated) TALL-104 cells were present in all of the organs and tissues examined. On day 3, the irradiated cells were no longer detectable in the PB and liver; and by day 5, they were detectable only in the BM. By contrast, as expected from previous work, the non-irradiated cells persisted in every organ (FIG. 3). These data show the ability of the modified (irradiated) TALL-104 cells to circulate and persist in SCID mouse tissues, at least for a few days after transfer.

Although γ-irradiation is used as an example, it is anticipated that other methods could be used to stop the growth of the cells, such as treatment with chemical agents that affect DNA synthesis, such as mitomycin C. The in vitro experiments demonstrating the loss of proliferative activity after irradiation and the persistence of cytotoxic activity are shown in FIGS. 4A to 4D and FIGS. 5A to 5F. FIGS. 4A to 4D indicate that (a) both TALL-104 cells and normal LAK cells lose irreversibly the ability to synthesize DNA and RNA within 1 day after γ-irradiation; (b) TALL-104 cells retain their cytotoxic activity after irradiation for at least 7 days, while normal LAK cells show a steady decline in cytotoxic activity from day 1 to day 7. FIGS. 5A to 5F show that the cytotoxic activity of lethally irradiated TALL-104 cells against three different tumor targets is similar to that of the non-irradiated counterpart whereas LAK cell cytotoxicity is highly radiosensitive.

Thus, in contrast to PBL from normal donors and primary leukemic cells [Kaufmann, et al, *J. Immunol.* 139:977–982 (1987)], both of which do not display cytotoxic activity in response to IL-2 after irradiation, the modified TALL-104 cell line maintains cytotoxic function upon lethal irradiation for at least seven days. Unlike the modified, irradiated TALL-104 cells, which can still respond very efficiently to activation by IL-2 and/or IL-12, irradiated LAK cells become unresponsive to IL-2 and IL-12. The loss of proliferative activity by TALL-104 cells upon irradiation is due to DNA damage and is known to be irreversible.

Therefore, irradiation of TALL-104 cells provides a modified cytotoxic cell line that has lost its proliferative ability and, therefore, the possibility of growing in an unrestrained fashion in the recipient organism. In fact, unlike the non-irradiated counterparts, modified γ-irradiated TALL-104 cells of this invention transplanted into SCID mice do not cause leukemia.

On the basis of all the characteristics described above, TALL-104 cells appropriately modified (i.e., cytokine activated and γ-irradiated) are highly effective and unable to proliferate and, therefore, suitable for use in adoptive immunotherapy of cancer and viral diseases in immunosuppressed HLA-mismatched recipients, as well as for eradication of residual malignant cells from patient's bone marrow (marrow purging). Unlike the CTL and LAK cells which are being used for adoptive therapy of cancer and viral diseases, the modified TALL-104 cell line is not patient-specific, but rather may be universally used in treatment of any HLA mismatched patient.

According to this invention, therefore, modified TALL-104 cells are prepared as follows. TALL-104 cells (ATCC CRL 11386) are exponentially grown in tissue culture in the presence of recombinant human (rh) IL-2. Before use, the cells are incubated overnight (i.e., for about 6 hours or more) in the presence of rh IL-2 (100 U/ml) and/or rh IL-12 (10 ng/ml). The cytokine-treated TALL-104 cells are then γ-irradiated using a Cesium source with gamma rays (at about 4,000 rads). The irradiation may be continued for a selected time, such as about 30 minutes. The resulting cell line is referred to as the modified TALL-104 cell line.

The preferred modalities of cancer treatment using the modified TALL-104 cells are the following two, as described herein. In one modality, a suitable number of modified TALL-104 cells are administered to a recipient host who receives immunosuppressive treatment with CsA following the criteria used for organ transplantation. Preferably, the mode of administration involves injecting the cells i.v. in saline. It is also anticipated that this treatment may be administered to a patient who may be already immunosuppressed due to his disease state. The evaluation of whether the patient's immune status is immunocompetent or severely compromised may be readily determined by one of skill in the art. Multiple injections of the modified (activated, lethally irradiated) TALL-104 cells are administered as deemed to be necessary, based on results obtained from preclinical studies with experimental animal systems.

The other modality of cancer treatment is marrow purging using the modified (i.e., IL-2/IL-12 activated, γ-irradiated) TALL-104 cells, as described above.

The following experiments demonstrate that the claimed modified cell line can be used effectively and safely as therapeutic agent both in clinical and veterinary practice. These experiments support the utility of the claimed invention, showing that the modified TALL-104 cell line is unique, being not patient specific, and endowed with broad anti-tumor and anti-viral cytotoxicity, without being cytotoxic for cells from normal tissues. These examples are illustrative only and do not limit the scope of the present invention.

EXAMPLE 1—TALL-104 CELL LINE

The origin and establishment of the IL-2-dependent TALL-104 cell line from the peripheral blood of a T-ALL patient, case CH-23 from the Children's Hospital of Philadelphia, is described in O'Connor et al, *Blood*, 77:1534–1545 (1991), incorporated by reference herein. Briefly, mononuclear cells from the leukemic sample were separated by Ficoll Hypaque gradient centrifugation and plated in 24-well Linbro plates [Flow Laboratory, McLean, VA]at a concentration of $1 \times 10^6$/mL in Iscove's modified Dulbecco's medium (IMDM) [Gibco, Grand Island, N.Y.] supplemented with 10% fetal bovine serum [Hycone, Logan, Utah]and antibiotics (complete medium). Recombinant human (rh) preparations of growth factors (IL-2, GM-CSF and IL-3) were added at specific concentrations.

The cells initially proliferated in the presence of IL-2 [Amgen], IL-3 and GM-CSF [Genetics Institute]and in the absence of added growth factors. However, after two months in culture, it became apparent that the cells in IL-2 proliferated much faster than those in the other conditions. These cells became established as an IL-2-dependent cell line, designated TALL-104, whereas those maintained in IL-3, GM-CSF, or no factor had a finite life span of about 6 months.

This TALL-104 cell line has a T cell phenotype (CD2, CD3, CD7, CD8, CD56), and has been in continuous culture since 1990 in the laboratory of the inventor, Dr. Santoli. The TALL-104 cells are maintained at 37° C. in 8%–10% $CO_2$ in IMDM (Gibco) supplemented with 10% fetal bovine serum. Biweekly addition of fresh medium containing rhIL-2 is required for optimal viability and continuous growth of TALL-104 cells; when these cells are propagated in the absence of this factor, they remain viable for a few weeks but lose cytotoxic activity gradually within a month [Cesano and Santoli, *In Vitro Cell. Dev. Biol.*, 28A:648–656 (1992)].

EXAMPLE 2—CYTOTOXICITY OF TALL-104 Cells

The MHC non-restricted tumoricidal activity of the IL-2 dependent TALL-104 cell line has been studied in detail, using standard $^{51}$Cr-release assays, as described [Cesano et al, *Blood*, 77:2463–2474 (1991); O'Connor et al, *Blood*, 77:1534–1545 (1991) and Cesano and Santoli, *In Vitro Cell. Dev. Biol.*, 28A:648–656 (1992)], incorporated by reference herein.

Prior to the assay, the effector cells are incubated in rhIL-2. IL-2-stimulated cells kill very efficiently a large variety of tumor cell lines and freshly separated leukemic samples but not cells from normal tissues (see Tables II and III). The TALL-104 cells can also be triggered by CD2- and CD3-specific monoclonal antibodies (mAb) to mediate cytotoxic activity against FcR+tumor cell lines [Cesano and Santoli, *In Vitro Cell. Dev. Biol.*, 28A:648–656 (1992)]. In addition, this cell line produces high levels of IFN-γ, TNF-α, TGF-β1 and GM-CSF on stimulation with antibodies recognizing CD2, CD3 and other surface molecules, tumor cells, IL-2, and IL-12 [Cesano and Santoli, *In Vitro Cell. Dev. Biol.*, 28A:657–662 (1992); Cesano et al, *J. Immunol.*, 151:2943 (1993)], incorporated by reference herein.

EXAMPLE 3—LACK OF CYTOTOXICITY OF TALL-104 CELL LINE AGAINST CELLS FROM NORMAL TISSUES.

The TALL-104 cell line, obtained as described herein, is not cytotoxic for cells from normal tissues and, therefore, can be used safely both ex vivo (marrow purging) and in vivo (adoptive transfer) because normal cells would not be killed. Failure of TALL-104 cells to kill cells from normal tissues is due to their inability to recognize and form conjugates with such targets.

Because both unirradiated and modified (irradiated) TALL-104 cells produce high levels of TNF-α and IFN-65 upon stimulation with IL-2 and IL-12 and/or exposure to tumor targets [Cesano and Santoli, *In Vitro Cell Dev. Biol.*, 28A:657–662 (1992b)], 2-week clonogenic assays were performed to exclude the possibility that such toxic lymphokines released by TALL-104 cells would impair the growth of hematopoietic precursors in bone marrow samples. FIGS. 7A to 7D show that in bone marrows admixed with TALL-104 cells at 0.1 and 1:1 ratios, the clonogenic growth of committed progenitors (CFU, BFU) was very similar to that of marrows incubated without TALL-104 cells.

Figure 8:
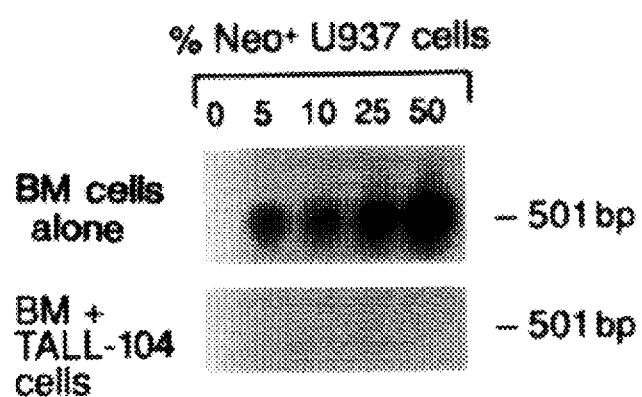
FIG. 8 is a gel illustrating the efficiency of modified TALL-104 cells in purging a bone marrow of leukemic cells (in this case the U937 cell line tagged with the Neomycin-resistance gene (Neo$^+$U937 cells). BM cells from a normal donor were mixed with different number of Neo$^+$U937 cells as indicated. IL-2/IL-12 activated, γ-irradiated (modified) TALL-104 cells were added to the mixture for 18 hours in the presence of 10 U/ml of DNAse I. Cellular DNA was extracted and subjected to PCR amplification using neomycin-resistant gene specific primers. An oligonucleotide probe specific for the amplified sequences was used to demonstrate the specificity of the PCR products.

Because the pluripotent $CD34^+$ stem cells are indispensable for a successful hematopoietic reconstitution, the number of $CD34^+$ cells was evaluated in T-cell depleted bone marrow samples before and after an 18 hour incubation with modified (γ-irradiated) TALL-104 cells. As determined by immunofluorescence analysis, the percentage of $CD34^+$ cells remained the same in the bone marrow samples incubated with TALL-104 cells (6–8% and 5.5–7.5% $CD34^+$ cells were found in untreated and TALL-104 treated bone marrow, respectively). Moreover, the colony-forming activity of CD34 cell-enriched cord blood samples was found to be totally unaffected upon an 18-hour incubation with lethally irradiated TALL-104 cells. All together, these results indicate that modified TALL-104 cells do not display any toxicity on normal stem cells nor on lineage-committed precursors and could, therefore, be used safely for bone marrow purging against leukemia. EXAMPLE 4—EFFICACY OF MODIFIED (LETHALLY IRRADIATED) TALL-104 CELLS IN MARROW PURGING To test the efficacy of modified, i.e., lethally irradiated, TALL-104 cells in marrow purging, the leukemia cell line U937 tagged with the neomycin-resistance gene was admixed at various ratios (0–50%) with cells from normal bone marrow, and modified, i.e., IL-2/IL-12 activated, γ-irradiated, TALL-104 cells were added at the ratio of 1:1 relative to bone marrow cells. The cell mixtures were then incubated for 18 hours and subjected to colony assays. No U937 cells could be detected microscopically after a 2-week culture in methylcellulose (Table V). PCR amplification of the Neomycin resistance gene 18 hours after the addition of TALL-104 cells to bone marrow/U937 samples confirmed the total absence of U937 cells from such samples at all E/T ratios used (FIG. 8).

TABLE V

| TALL-104/BM Ratio | %U937 Cells in the Bone Marrow | Number of U937 Colonies |
|---|---|---|
| 0/1 | 0 | 0 |
| 0/1 | 5 | 19 |
| 0/1 | 10 | 40 |
| 0/1 | 25 | 112 |
| 0/1 | 50 | 235 |
| 1/1 | 0 | 0 |
| 1/1 | 5 | 0 |
| 1/1 | 10 | 0 |
| 1/1 | 25 | 0 |
| 1/1 | 50 | 0 |

In conclusion, these studies (Examples 3 and 4) indicate that modified, i.e., lethally irradiated, TALL-104 cells represent a unique cell system to design clinically safe and highly effective marrow purging strategies for future ABMT programs. Moreover, this purging strategy for the elimination of MRD in leukemia is applicable to any form of cancer displaying bone marrow involvement, including neuroblastoma in children and breast carcinoma in adult patients.
EXAMPLE 5—ANTITUMOR EFFICACY OF MODIFIED TALL-104 CELLS IN ADOPTIVE IMMUNOTHERAPY The following experiments carried out in experimental animals show that the modified TALL-104 cells of this invention can be used effectively in adoptive immunotherapy treatment of cancer. These treatments are demonstrated both in severe combined immunodeficient (SCID) mice, which is an animal model for cancer treatment accepted by one of skill in the art, and in immunocompetent mice treated with CsA to prevent allograft rejection.

For use in the following experiments, the TALL cells of the invention were modified as follows. The cells were exponentially grown in tissue culture in the presence of IL-2. Before use, the cells were washed, incubated overnight in the presence of IL-2 (100 U/ml) and/or IL-12 and γ-irradiated using a Cesium source with gamma rays (4000 rads).

Figure 9:
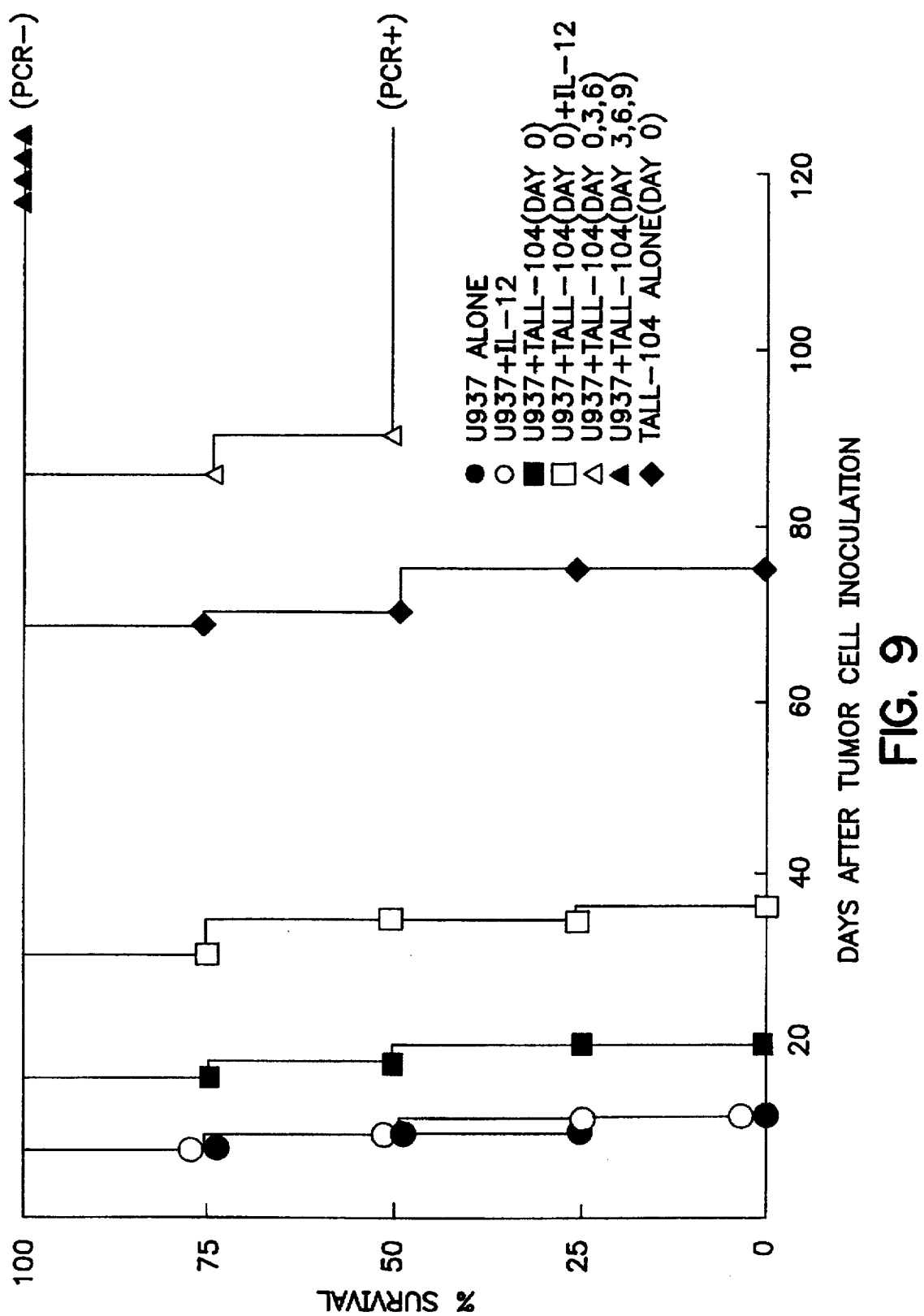
FIG. 9 is a graph illustrating the survival of U937-engrafted SCID mice after treatment with IL-2 activated, non-irradiated TALL-104 cells. Mice were injected i.p. with $10^7$ U937 cells. TALL-104 cells, activated ex vivo with 100 U/ml rh IL-2, were injected i.p. ($2 \times 10^7$ cells) at various intervals, as indicated. rh IL-12 was given to one group of mice i.p. for 7 days at the dose of 1 µg/day.

A. Prevention and regression of acute myelogenous leukemia (AML) in SCID mice SCID mice were implanted i.p. with the human myeloid leukemia cell line U937 [ATCC CRL 1593]. These cells are very aggressive and kill mice in 21 days if injected i.v. [Cesano et al, *Oncogene*, 7:827 (1992)]or only 8–10 days if injected i.p. Treatment with modified TALL-104 cells was done at different times after injection of the AML target, and the survival of the mice was determined for a span of several months, as indicated in FIG. 9. Survivors, showing no symptoms after a 6-month observation period, were sacrificed and the presence of human cells (both effectors and targets) in the BM was evaluated by PCR analysis using primers specific for human ALU-DNA sequences. The most remarkable finding in the experiments presented in FIG. 9 is that multiple transfers, at short intervals, of modified, IL-2-activated TALL-104 cells cured 50% of the mice from an advanced stage of leukemia. In fact, of the mice injected with TALL-104 cells three times starting on day 3, when U937 cells had already infiltrated the PB, two developed AML and died 3 months later, and two remained clinically and morphologically free of disease for at least 6 months (FIG. 9). PCR amplification of human ALU-DNA sequences provided molecular evidence for the persistence of residual cells in the BM of the survivors. Whether these cells represented TALL-104 effectors or U937 targets could not be determined in this set of experiments. Importantly, complete abrogation of AML, as monitored both clinically and by PCR analysis, was achieved by repeated injection of the effector cells on days 0, 3, and 6 (FIG. 9).

When the modified TALL-104 cells were injected at the same time as U937 cells on day 0 (i.e., without any delay) but on the opposite flank, PCR amplification of human ALU-DNA sequences in the BM of these mice, electively sacrificed 6 months from treatment, demonstrated that both types of leukemic populations, the myeloid target and the lymphoid effector, were eliminated from the mouse tissues. Another interesting observation from the experiments shown in FIG. 9 is that administration of low doses of rh IL-12 (1 µg/d for 7 d) in conjunction with TALL-104 cells at the time of U937 cell challenge induced a significantly longer survival in the animals, as compared to mice receiving U937 and modified (IL-2 activated) TALL-104 cells alone, without rh IL-12. Overall, the findings in FIG. 9 indicate that, depending on the tumor load at the time of treatment, adoptive transfer of modified TALL-104 cells either induced complete abrogation of AML or inhibited significantly tumor growth even during advanced stages of the disease. Thus, the extent of tumor reduction appears to reflect the E/T ratio at the time of treatment.

Figure 10A:
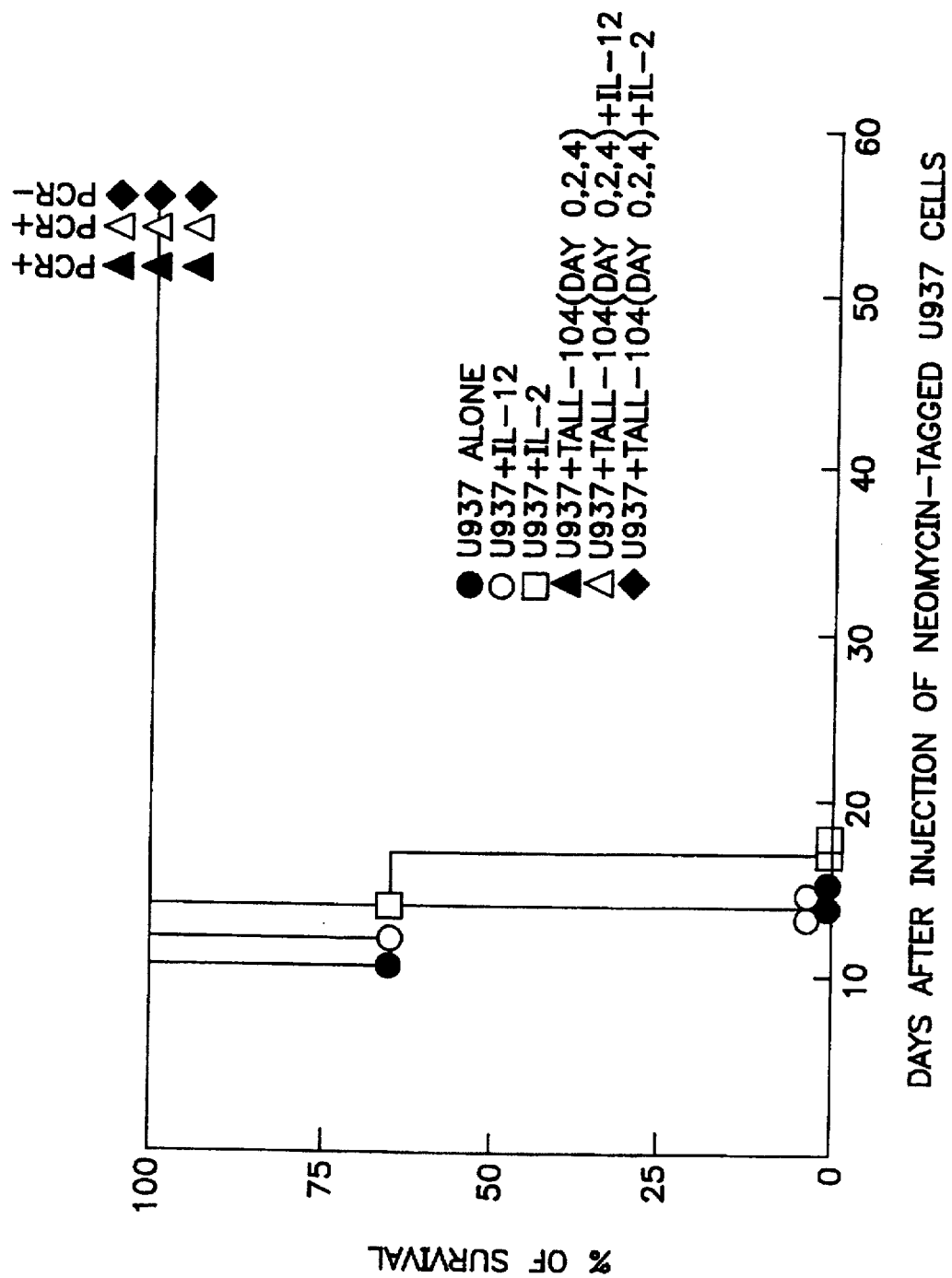
FIG. 10A is a graph illustrating the survival of SCID mice engrafted i.p. with neomycin-tagged U937 cells and treated with modified (γ-irradiated) TALL-104 cells. Mice received $10^7$ U937 cells on day 0, and modified TALL-104 cells ($2 \times 10^7$) three times on alternate days, starting from the day of tumor challenge. Both control (U937 injected) and experimental (U937/TALL-104 injected) mice received IL-2 or IL-12 daily for 1 week.
Figure 10B:
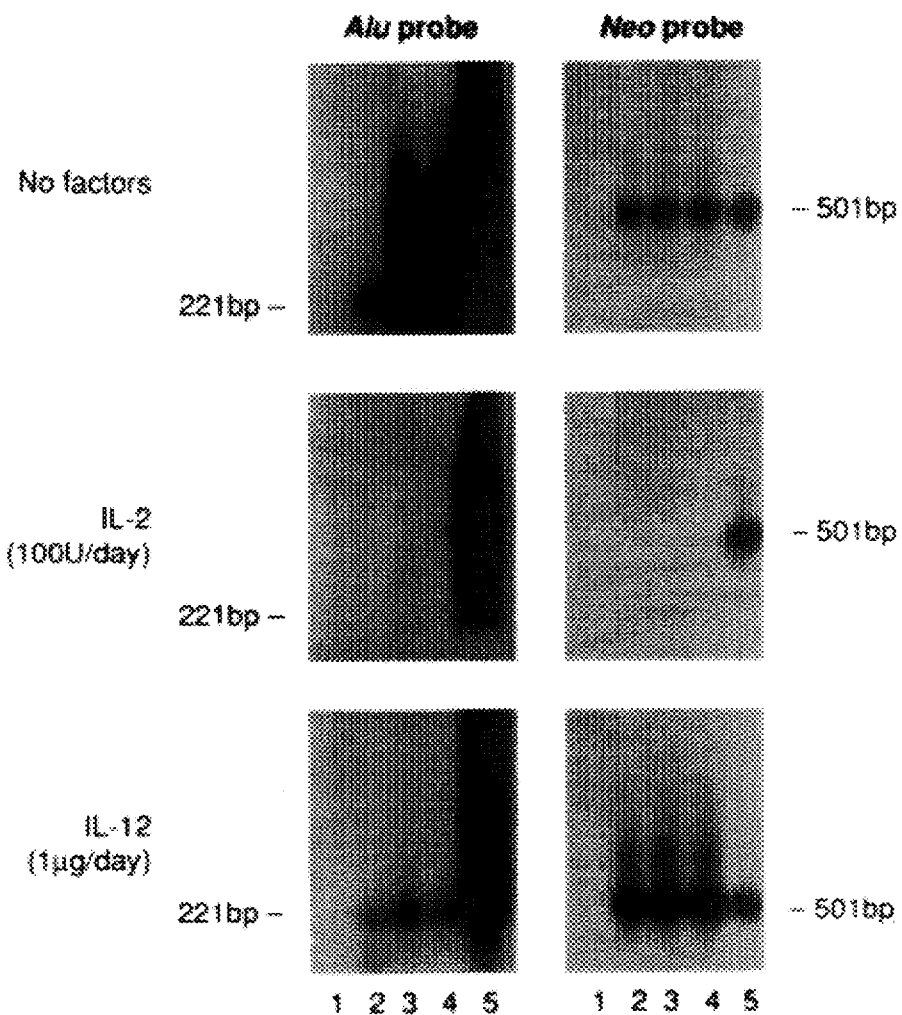
FIG. 10B is a gel illustrating the PCR detection (as obtained on gels) of residual AML in SCID mice upon adoptive transfer of modified (γ-irradiated) TALL-104 cells. Mice received U937 and modified TALL-104 cells and cytokines, as outlined above in FIG. 10A. Cellular DNA was extracted on day 55 from the BM of asymptomatic animals and subjected to PCR amplification using primers specific for both human ALU sequences and the neomycin resistance gene. DNAs were visualized with ethidium bromide after electrophoresis in 2% agarose gels. Southern blots were hybridized with the indicated oligo probes. Lanes 1 and 5 represent the negative (water) and positive (neomycin$^+$ U937 cells) controls, respectively. Lanes 2–4 represent the experimental mice, which received both U937 and γ-irradiated TALL-104 cells, in conjunction or not with cytokines.

Based on the observations that lethally irradiated TALL-104 cells express tumoricidal activity in vitro (FIGS. 4A to 4D and 5A to 5F) and are able to circulate in SCID mouse tissues (FIG. 3), experiments were performed to determine the extent to which TALL-104 cells modified by γ-irradiation display anti-tumor effects in the SCID/U937 model. To have an objective way for detection of MRD in the treated mice, the U937 clone tagged with the neomycin-resistance gene was used in these experiments. FIGS. 10A and 10B show the survival curve and PCR data, respectively, from an experiment in which SCID mice were challenged with Neo$^+$ U937 cells and treated, or not, with the modified irradiated TALL-104 cells. The effectors were transferred on alternate days ($2 \times 10^7$, i.p.), starting from the day of U937 cell challenge: as also indicated in the experiment shown in FIG. 9, TALL-104 cells were co-injected with U937 cells on day 0 in the opposite flank. Modified TALL-104 cells were transferred either alone or in conjunction with rh IL-2 (100 &/d) or rh IL-12 (1 µg/d), daily for 7 days. All mice receiving only U937 cells ($10^7$ i.p.), either alone or in combination with daily administration of IL-2 and IL-12 for 1 week, died between days 11 and 16 (FIG. 10A). In contrast, mice treated with modified irradiated TALL-104 cells, alone or in conjunction with the cytokines, remained disease-free (looked clinically well and showed no signs of disease) for at least 2 months (FIG. 10A). At this time, PCR amplification of human ALU-DNA sequences demonstrated the presence of human cells in the BM of mice treated with modified TALL-104 cells alone or treated with modified TALL-104 cells and rh IL-12 (FIG. 10B). PCR analysis using neomycin-specific primers confirmed the presence of residual U937 cells in the same samples (FIG. 10B). By contrast, administration of rh IL-2 to modified TALL-104 cell-treated mice resulted in the total disappearance of molecularly detectable leukemic cells, using either type of primers (FIG. 10B). These data indicate that, in vivo, the modified γ-irradiated TALL-104 cells are still responsive to low doses of rh IL-2, whereas higher doses of rh IL-12 may be desirable.

B. Inhibition of human glioblastoma growth in SCID mice

SCID mice were engrafted subcutaneously with the human U-87 MG glioblastoma cell line [ATCC HTB 14]using conventional techniques. This cell line induces a local tumor, ultimately resulting in skin ulceration within 4 weeks.

The modified (IL-2 or IL-12 activated, γ-irradiated) TALL-104 cells were adoptively transferred to the SCID mice by injection at the tumor site. Control animals received only PBS. For the smaller tumor (2 mm), therapy was applied by local injection 3×, every 10 days. For the larger tumor (5 mm), therapy was applied by local injection 5×, on alternate days. In another set of experiments, the irradiated killers were transferred three times on alternate days starting from the day of U87 MG cell challenge.

The results are provided in Table VI. Column 1 provides the tumor size at the time of modified TALL-104 cell transfer. Column 2 indicates whether modified TALL-104 cells or just PBS were administered. Column 3 provides the tumor load at the time the mice were sacrificed. Column 4 provides the percentage of tumor reduction in modified TALL-104-injected animals as compared to control mice receiving only PBS.

TABLE VI

Reduction of subcutaneous growth of a human glioblastoma in SCID mice upon adoptive transfer of modified (γ-irradiated and IL-2 Or IL-12 treated) TALL-104 cells.

| Tumor size (mm) | Therapy | Tumor load (mg) | % Tumor Reduction |
|---|---|---|---|
| 2 | PBS | 662 ± 40* | |
|   | TALL-104 | 225 ± 40 | −75% |
| 5 | PBS | 1062 ± 103 | |
|   | TALL-104 | 535 ± 110 | −50% |
| 0 | PBS | 784 ± 228 | 100% |
|   | TALL-104 | 0 | |

*Mean ± standard deviation from three mice.

As shown in the table above, mice injected at the tumor site with modified (cytokine treated and γirradiated) TALL-104 cells displayed a 50–100% reduction of tumor load (as compared to control mice receiving only PBS), depending on the size of the original tumor when therapy was started.

C. Treatment of cyclosporin A-treated immunocompetent mice bearing syngeneic leukemia To investigate the feasibility of using modified (lethally irradiated) TALL-104 cells of the invention in MHC incompatible, immunocompetent recipients, the following experiment was conducted.

TALL-104 cells were obtained as described in Example 1, grown in tissue culture in the presence of IL-2 and then modified by γ-irradiation as follows. The cells were washed in 50 ml of IMDM medium, incubated at 37° C. overnight in the presence of 100 U/ml IL-2 and 10 ng/ml IL-12, and irradiated using a Cesium source with gamma rays (4000 rads).

These cells were injected intraperitoneally (i.p.) in cyclosporin A (CsA)-treated B6D2F1 mice. PCR analysis demonstrated that when administered to CsA-treated animals, TALL-104 cells were able to persist in various organs for at least 7 days. In contrast, in mice that were not treated with CsA, TALL-104 cells were detectable in their peripheral blood (PB), bone marrow (BM) and lung (but not spleen) only until day 3.

To study the anti-tumor efficacy of irradiated TALL-104 cells in CsA-treated B6D2 mice, the following experiment was performed:

$10^7$ cells of a murine B lymphoid leukemia cell line (70z) were engrafted intraperitoneally into syngeneic immunocompetent three week old male mice using conventional techniques. The mice were randomly assigned to three groups, five per group.

In a first group, the mice were treated from the day of implant of 70z cells (day 0) with multiple i.p. transfers of $2 \times 10^7$ of the modified irradiated TALL-104 cells on alternate days for 10 days in conjunction with daily i.p. administration of 10 mg/kg CsA once a day. Neither IL-12 nor IL-2 were administered to the mice.

In a second group (control), the leukemia-bearing mice were treated only with CsA for 10 days. No TALL-104 cells were introduced into these mice.

In a third group (control), the leukemia-bearing mice were treated with multiple transfers of modified irradiated TALL-104 cells on alternate days for 10 days, as described above, with the exception that no CsA was administered.

All five mice treated with multiple transfers of modified irradiated TALL-104 cells on alternate days for 10 days in conjunction with daily administration of CsA were clinically cured (group 1). PCR analysis performed 3 months later on all five asymptomatic mice provided molecular evidence for the absence of 70z leukemia in their tissues.

In contrast, both control groups of leukemia-bearing mice treated only with CsA (without modified TALL-104 cells) or only with modified TALL-104 cells (without CsA), died of leukemia within 12 days (groups 2 and 3).

This data indicates that modified (lethally irradiated) TALL-104 cells are not rejected and function effectively in immunocompetent recipients receiving immunosuppressive treatment (CsA). The fact that the TALL-104 treated mice remained healthy for at least 3 months after treatment indicates that the TALL-104 cells do not proliferate in the mice and do not cause toxic effects.

D. Induction of specific anti-tumor immunity by TALL-104 cells in immunocompetent mice bearing syngeneic leukemia In another experiment, anti-tumor efficacy and induction of a state of specific anti-tumor immunity was observed upon administration of TALL-104 cells (prepared as described above) in B6D2F1 mice bearing syngeneic leukemia. As in the experiments described immediately above, the 70Z pre-B ALL cell line was used.

70Z cells could be detected in the mouse tissues by PCR amplification of their specific CDRIII region: specifically, they were detectable in the BM as early as 2 days after 70Z cell transfer, in the PB starting from day 3, and in most organs including the central nervous system starting from day 5.

At different stages of leukemic infiltration (day 0, 2, 3, 5), mice were immunosuppressed with CsA (10 mg/Kg i.p.), and IL-2-treated, irradiated TALL-104 cells were injected ($2 \times 10^7$ i.p.) on alternate days for a total of 5 times.

The results obtained showed that modified TALL-104 cell treatment was able to completely prevent or reverse 70Z cell growth in the animals, depending on the time of initiation of therapy (early versus advanced stages, respectively). Mice that were still asymptomatic after 6 months were also disease free at the molecular level, as shown by PCR.

Importantly, rechallenge of these animals with high doses of 70Z cells ($2 \times 10^7$ i.p.) did not result in leukemia, indicating the ability of their immune system to recognize and reject the original tumor cells. It, therefore, appears that the IL-2-stimulated, gamma-irradiated TALL-104 cells were not only able to cause disease regression in these animals, but also to induce a specific state of anti-tumor immunity. This finding indicates that upon TALL-104 cell treatment, the host can be protected against relapses due to residual disease through the activation of his own immune cells.

EXAMPLE 6—ABILITY OF MODIFIED (LETHALLY IRRADIATED) TALL-104 CELLS TO KILL DOG LYMPHOMAS AND CAT LEUKEMIAS IN THE SCID MOUSE MODEL

Figure 11A:
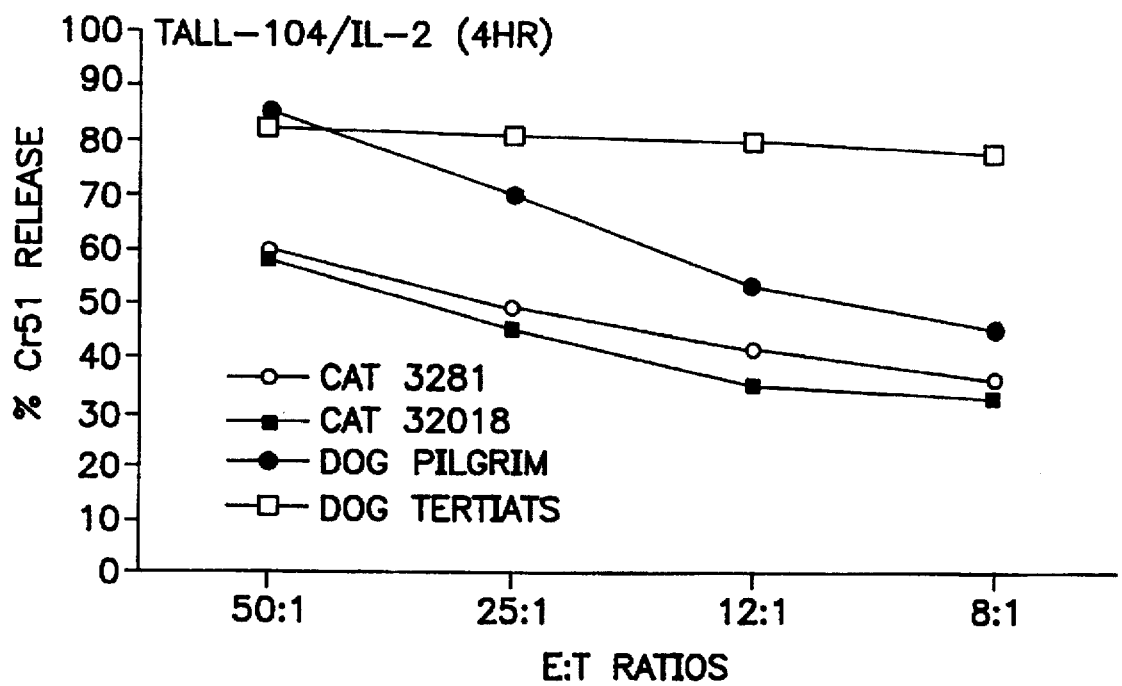
FIG. 11A is a graph showing the ability of modified (IL-2 activated) TALL-104 cells to lyse cat leukemia (Cat 3281 and Cat 3201B) cell lines and dog lymphoma (Pilgrim and Tertiat's) cell lines in a 4 hour $^{51}$Cr release assay using various E/T ratios.
Figure 11B:
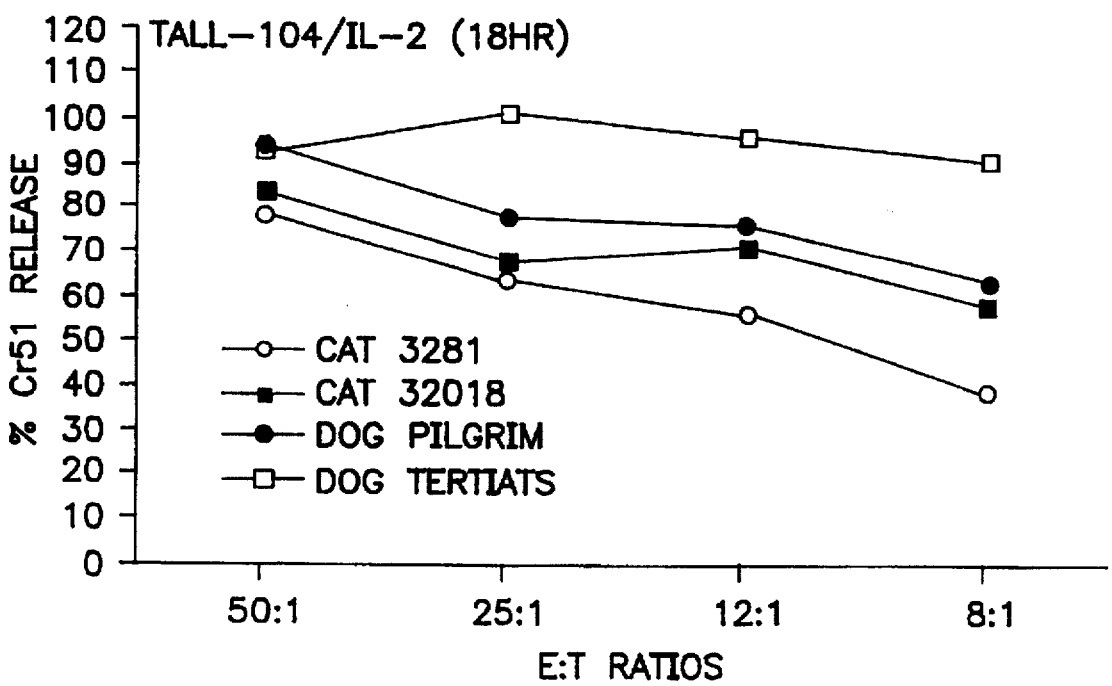
FIG. 11B is a graph showing the ability of modified (IL-2 activated) TALL-104 cells to lyse cat leukemia (Cat 3281 and Cat 3201B) cell lines and dog lymphoma (Pilgrim and Tertiat's) cell lines in a 18 hour $^{51}$Cr release assay using various E/T ratios.
Figure 12A:
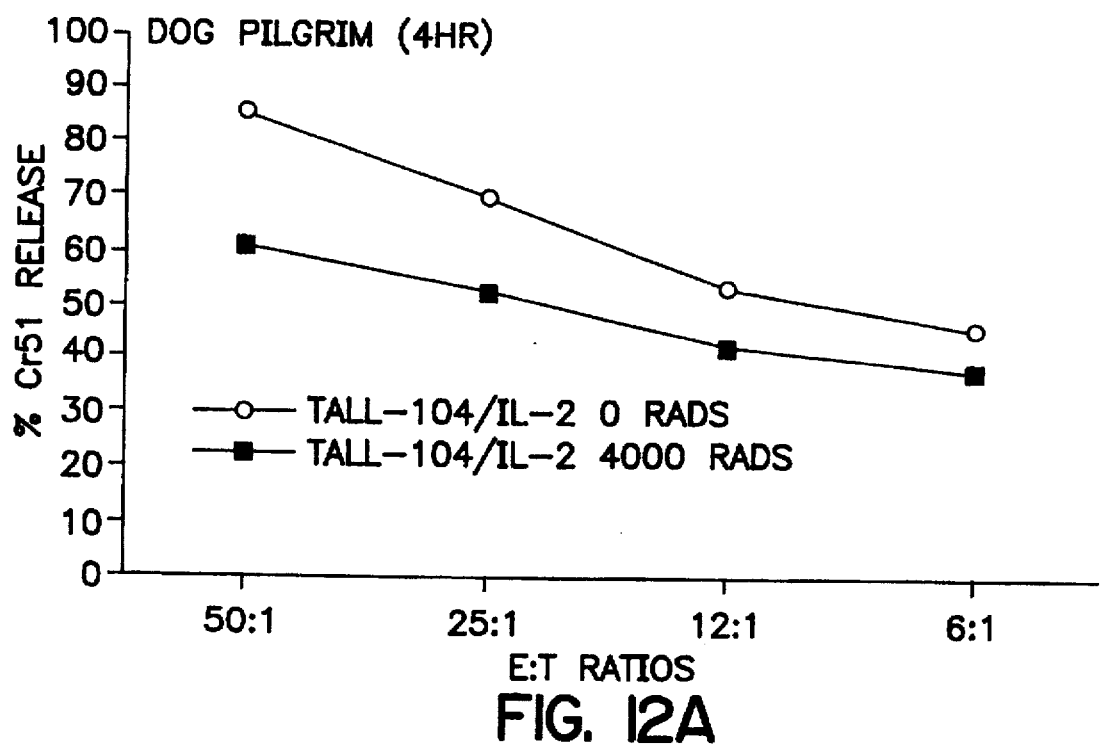
FIG. 12A is a graph demonstrating the ability of modified (IL-2 activated, lethally irradiated) (■) TALL-104 cells to lyse a dog lymphoma (Pilgrim) cell line with similar efficiencies as unirradiated (○) TALL-104 cells. The $^{51}$Cr release assays were done for 4 hours at various E/T ratios.
Figure 12B:
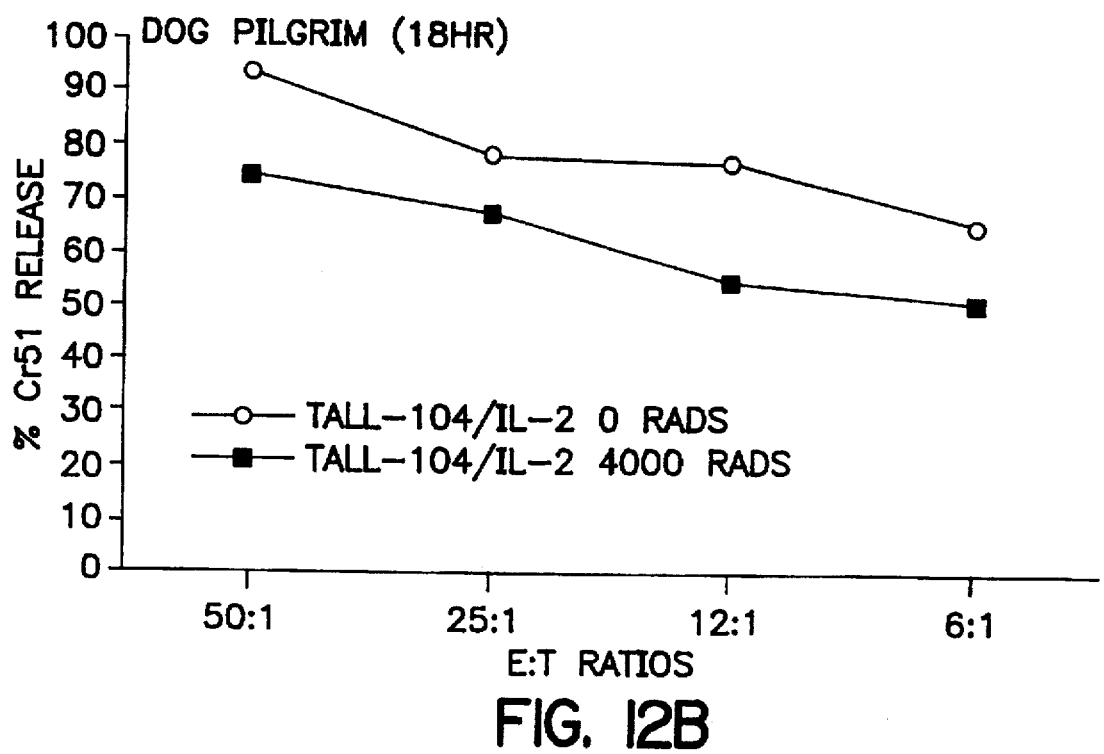
FIG. 12B is a graph demonstrating the ability of modified (IL-2 activated, lethally irradiated) (■) TALL-104 cells to lyse a dog lymphoma (Pilgrim) cell line with similar efficiencies as unirradiated (○) TALL-104 cells. The $^{51}$Cr release assays were done for 18 hours at various E/T ratios.

Four cell lines established from either dog lymphomas (Pilgrim and Tertiats) or cat leukemias (CAT 3281 and CAT 3201B) were analyzed for susceptibility to TALL-104 cell killing in a $^{51}$Cr-release assay. FIGS. 11A and 11B show that all four cell lines are highly susceptible to TALL-104 lysis within 4 hours from the interaction with the effector cells (top panel) and are killed 80–100% within 18 hours (bottom panel) even at low effector/target ratios. FIGS. 12A and 12B show that modified, lethally irradiated TALL-104 cells kill these targets with an efficiency similar to the unirradiated cells as measured both in a 4-hour (top) and 18-hour (bottom) $^{51}$Cr-release assay.

Because all four of the above cell lines can be engrafted in SCID mouse tissues, studies were performed to analyze the ability of modified lethally irradiated TALL-104 cells to control the growth of cat and dog malignancies in these chimeric SCID models. Results indicated that, indeed, modified TALL-104 cells can, in appropriate experimental conditions, cure SCID mice bearing such tumors.

EXAMPLE 7—ANTI-TUMOR EFFICACY OF TALL-104 CELLS IN CANINES WITH SPONTANEOUS REFRACTORY TUMORS

Recent experiments in dogs with spontaneous refractory (end-stage) tumors have revealed both the safety and efficacy of the use of cytokine (IL-2) stimulated, irradiated TALL-104 cells in veterinary practice. The following example is provided below in which treatment with TALL-104 cells cured a dog with terminal cancer and induced a permanent anti-tumor immunity by activating the dog's immune cells against his own tumor.

An 8-year-old Scottish Terrier presented with end-stage malignant histiocytosis. The prognosis was grave due to the progressive disease and lack of response to chemotherapeutics. Prior to TALL-104 treatment, the dog had several large lymph nodes, and had developed left inguinal and right axillary lymphadenopathy.

After the dog was treated with 6 infusions of IL-2-stimulated, gamma-irradiated TALL-104 cells ($10^8$ cells/kg) on alternate days, the right axillary lymph node had completely regressed. At this time, the dog demonstrated significant improvement in overall attitude and well-being. Objective and measurable anti-tumor effects were observed after two more treatments, with complete regression of the axillary lymph node and >50% decrease in the inguinal lymph nodes and neck mass. Thoracic radiographs were negative for lymphadenopathy or pulmonary infiltrate. CBC and chemscreen were normal throughout the treatment course. TALL-104 therapy was ended at this point.

Two weeks later, new subcutaneous nodules were found upon reexamination on the left hind and front legs (2.0 cm) of the dog. It was decided to surgically remove these nodules to test their susceptibility to TALL-104 cell lysis in $^{51}$Cr-release assays. However, 2 days later, the lesions had spontaneously regressed and surgical removal was not possible.

Blood was drawn and Ficoll-Hypaque-separated lymphocytes were tested for natural killer (NK) activity against human tumor targets, including TALL-104 cells. Results showed that the dog's lymphocytes were highly activated, being able to kill both NK-susceptible (U937) and NK-resistant (T-ALL) human targets. Interestingly, however, his PBL failed to lyse TALL-104 cells, indicating lack of specific cytotoxic T lymphocyte (CTL) responses against the xenogeneic effectors.

When blood was drawn again 10 days later, NK activity had significantly declined. The overall in vitro data indicated the presence of an activated immunological state in the dog at the time of spontaneous regression of the metastatic lesions, which could explain its ability to fight against relapses without further treatments. No previous tumor biopsies were available from the dog to test tumor-specific CTL activity. Continued improvement was observed later on with complete regression of the earlier lesions. This dog continues to be in complete remission five months after the end of TALL-104 therapy.

Examples 5D and 7 demonstrate another attribute of the TALL-104 cells of this invention, that is, that passive treatment with the cells appears to induce an anti-tumor specific immune response in the treated patient similar to that expected in response to a vaccine. This results in effective elimination of residual disease by the patient's immune system in the absence of additional chemotherapy.

Treatment with TALL-104 cells therefore can complement cancer treatment with conventional chemotherapeutic agents and may even reduce the amount of chemotherapy a patient will require in the treatment of a cancer. Additionally the anti-tumor effect of TALL-104 administration also appears to be effective with cancers which are, or have become, resistant to at least some types of chemotherapy.

The cell line of this invention has been deposited in the culture collection of the American Type Culture Collection, in Rockville, Maryland on Jun. 15, 1993, and identified there as "TALL-104". The cell line was tested and determined to be viable on Jun. 18, 1993. This culture was assigned ATCC Accession No. CRL 11386. The ATCC has agreed to maintain the culture for a period of 30 years from deposit date, or until at least five years after the most recent request for a sample, whichever is longer.

Numerous modifications and variations of the present invention are included in the above-identified specification and are expected to be obvious to one of skill in the art. Such modifications and alterations to the methods of the present invention are believed to be encompassed in the scope of the claims appended hereto.

What is claimed is:

1. A method for adoptive therapy useful in the treatment of cancer comprising administering to a mammalian patient an effective amount of a TALL-104 cell, ATCC Accession No. CRL11386, which has been modified by treatment in vitro with one or a combination of IL-2 and IL-12 to enhance its cytotoxicity and gamma-irradiated at a dose suitable to irreversibly arrest cell proliferation but retain its cytotoxic activity in vitro and in vivo, in combination with an effective dose of an immunosuppressive agent that will not suppress the cytotoxic function of the cell but will suppress the patient's immune function.

2. The method according to claim 1 wherein said modified TALL-104 cell is characterized by enhanced cytotoxic activity in vitro and in vivo, irreversibly arrested cell proliferation resulting from exposure to a dose of 4000 rads of gamma-irradiation, and the capacity to migrate in vivo to different tissues.

3. The method according to claim 1 wherein said immunosuppressive agent is selected from the group consisting of Cyclosporin A and glucocorticoids.

4. The method according to claim 1 wherein said cancer is a non-hematological malignancy, a solid tumor, or a hematological malignancy.

5. A veterinary method for treating feline malignancy comprising administering to a feline an effective amount of a TALL-104 cell, ATCC Accession No. CRL11386, which has been modified by treatment in vitro with one or a combination of IL-2 and IL-12 to enhance its cytotoxicity and gamma-irradiated at a dose suitable to irreversibly arrest cell proliferation but retain its cytotoxic activity in vitro and in vivo, in combination with an effective dose of an immunosuppressive agent that will not suppress the cytotoxic function of the TALL-104 cell but will suppress the feline's immune response.

6. A veterinary method for treating canine malignancy comprising administering to a canine an effective amount of a TALL-104 cell, ATCC Accession No. CRL11386, which has been modified by treatment in vitro with one or a combination of IL-2 and IL-12 to enhance its cytotoxicity and gamma-irradiated at a dose suitable to irreversibly arrest cell proliferation but retain its cytotoxic activity in vitro and in vivo, in combination with an effective dose of an immunosuppressive agent that will not suppress the cytotoxic function of the TALL-104 cell but will suppress the canine's immune response.

7. The method according to claim 1, wherein said suitable dose is about 4000 rads.

8. The method according to claim 1 wherein said modified TALL-104 cell is in a suitable pharmaceutical carrier.

* * * * *